US009709769B2

(12) United States Patent
Rohani et al.

(10) Patent No.: US 9,709,769 B2
(45) Date of Patent: Jul. 18, 2017

(54) METHODS FOR OPTICALLY ALIGNING LIGHT COLLECTION COMPONENTS AND OPTICALLY ALIGNED LIGHT COLLECTION SYSTEMS THEREOF

(71) Applicant: Becton, Dickinson and Company, Franklin Lakes, NJ (US)

(72) Inventors: Mina Rohani, Seattle, WA (US); Timothy Wayne Petersen, Seattle, WA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 51 days.

(21) Appl. No.: 14/925,616

(22) Filed: Oct. 28, 2015

(65) Prior Publication Data
US 2016/0170168 A1 Jun. 16, 2016

Related U.S. Application Data

(60) Provisional application No. 62/090,248, filed on Dec. 10, 2014.

(51) Int. Cl.
*G02B 7/02* (2006.01)
*G02B 7/00* (2006.01)
(Continued)

(52) U.S. Cl.
CPC ......... *G02B 7/022* (2013.01); *G01N 15/1434* (2013.01); *G01N 15/147* (2013.01);
(Continued)

(58) Field of Classification Search
CPC ........ G02B 7/022; G02B 7/003; G02B 15/06; G02B 7/14; G01N 15/1434; G01N 2015/1452
See application file for complete search history.

(56) References Cited

U.S. PATENT DOCUMENTS 3,960,449 A 6/1976 Carleton et al.
4,347,935 A 9/1982 Merrill
(Continued)

FOREIGN PATENT DOCUMENTS

WO WO 2012/149174 A2 11/2012
WO WO 2014/176366 A1 10/2014

OTHER PUBLICATIONS

Becton, Dickinson and Company "BD FACSCalibur Instructions for Use", Part No. 643271, Rev. A, Nov. 2007, 238 pages. Available online: http://static.bdbiosciences.com/documents/BD_FACSCalibur_instructions.pdf.
(Continued)

*Primary Examiner* — Sang Nguyen
(74) *Attorney, Agent, or Firm* — Khin K. Chin; Bret E. Field; Bozicevic, Field & Francis LLP

(57) ABSTRACT

Aspects of the present disclosure include methods for optically aligning components of a light collection system. Methods according to certain embodiments include coupling a connector having a first lens to an optical adjustment component having a second lens by connecting a first magnet and first aligner positioned on the connector to a second magnet and second aligner positioned on the optical adjustment component such that connecting the first magnet and first aligner to the second magnet and second aligner is sufficient to position the connector lens to be optically concentric with the optical adjustment component lens. Light collection systems optically aligned by the subject methods including flow cell nozzles optically aligned with an optical adjustment component are also described. Systems and methods for measuring light emitted by a sample (e.g., in a flow stream) are also provided.

19 Claims, 4 Drawing Sheets

(51) Int. Cl.
*G01N 15/14* (2006.01)
*G01N 15/10* (2006.01)

(52) U.S. Cl.
CPC . *G01N 15/1459* (2013.01); *G01N 2015/1006* (2013.01); *G01N 2015/149* (2013.01); *G01N 2015/1452* (2013.01); *G02B 7/003* (2013.01)

(56) References Cited

U.S. PATENT DOCUMENTS

| | | | |
|---|---|---|---|
| 4,667,830 A | | 5/1987 | Nozaki, Jr. et al. |
| 4,704,891 A | | 11/1987 | Recktenwald et al. |
| 4,770,992 A | | 9/1988 | Van Den Engh et al. |
| 5,030,002 A | | 7/1991 | North, Jr. |
| 5,040,890 A | | 8/1991 | North, Jr. |
| 5,047,321 A | | 9/1991 | Loken et al. |
| 5,245,318 A | | 9/1993 | Tohge et al. |
| 5,317,162 A | | 5/1994 | Pinsky et al. |
| 5,464,581 A | | 11/1995 | Van Den Engh |
| 5,483,469 A | | 1/1996 | Van Den Engh et al. |
| 5,602,039 A | | 2/1997 | Van Den Engh |
| 5,620,842 A | | 4/1997 | Davis et al. |
| 5,627,040 A | | 5/1997 | Bierre et al. |
| 5,643,796 A | | 7/1997 | Van Den Engh et al. |
| 5,700,692 A | | 12/1997 | Sweet |
| 6,084,726 A | * | 7/2000 | Lee .................... G11B 7/0933 359/813 |
| 6,372,506 B1 | | 4/2002 | Norton |
| 6,809,804 B1 | | 10/2004 | Yount et al. |
| 6,813,017 B1 | | 11/2004 | Hoffman et al. |
| 6,821,740 B2 | | 11/2004 | Darzynkiewicz et al. |
| 7,110,192 B2 | | 9/2006 | Sauter et al. |
| 7,129,505 B2 | | 10/2006 | Oostman, Jr. et al. |
| 7,201,875 B2 | | 4/2007 | Norton et al. |
| 7,544,326 B2 | | 6/2009 | Norton et al. |
| 8,140,300 B2 | | 3/2012 | Dunne et al. |
| 8,233,146 B2 | | 7/2012 | Chen |
| 8,320,753 B2 | * | 11/2012 | Lee ........................ G03B 17/00 348/208.11 |
| 8,753,573 B2 | | 6/2014 | Van Den Engh et al. |
| 8,975,595 B2 | | 3/2015 | Norton et al. |
| 8,992,835 B2 | | 3/2015 | Van Den Engh et al. |
| 9,092,034 B2 | | 7/2015 | Vrane et al. |
| 9,095,494 B2 | | 8/2015 | Warner et al. |
| 9,097,640 B2 | | 8/2015 | Goldberg et al. |
| 2002/0159027 A1 | * | 10/2002 | Tai ........................... B24B 9/146 351/159.19 |
| 2005/0063695 A1 | | 3/2005 | Kameyama |
| 2005/0134850 A1 | | 6/2005 | Rezachek et al. |
| 2008/0187301 A1 | * | 8/2008 | Takahashi ................ G03B 5/00 396/55 |
| 2009/0128637 A1 | * | 5/2009 | Noji ........................ G03B 5/00 348/208.1 |
| 2010/0232161 A1 | * | 9/2010 | Aschwanden ........... G02B 3/14 362/278 |
| 2010/0295952 A1 | * | 11/2010 | Oh ........................ G03B 17/00 348/208.4 |
| 2011/0007202 A1 | * | 1/2011 | Chiang .................. G02B 7/102 348/345 |
| 2012/0268648 A1 | * | 10/2012 | Yang .................... H04N 5/2252 348/360 |
| 2013/0141799 A1 | * | 6/2013 | Li .......................... G02B 7/102 359/695 |
| 2013/0150669 A1 | * | 6/2013 | Deng ................. A61B 1/00112 600/109 |
| 2014/0091204 A1 | * | 4/2014 | Ezawa ..................... G02B 7/08 250/208.1 |
| 2014/0320861 A1 | * | 10/2014 | van den Engh ....... G01N 21/85 356/440 |

OTHER PUBLICATIONS

Becton, Dickinson and Company "BD FACSAria II User's Guide", Part No. 644832, Rev. A, Mar. 2009, 354 pages. Available online: http://static.bdbiosciences.com/documents/BD_FACSAria_II_User_Guide.pdf.

Becton, Dickinson and Company "BD LSRFortessa Cell Analyzer User's Guide", Part No. 23-11093-00, Rev. A, Mar. 2010, 194 pages. Available online: http://static.bdbiosciences.com/documents/BD_LSRFortessa_cell_analyzer_user_guide.pdf.

Becton, Dickinson and Company "BD Influx™ Cell Sorter User's Guide", Part No. 23-11543-00, Rev. 01, Apr. 2011, 378 pages. Available online: http://static.bdbiosciences.com/documents/BD_Influx_User_Guide.pdf.

Becton, Dickinson and Company "BD Accuri™ C6 Flow Cytometer Instrument Manual", Part No. 7820018, Rev. 2, 2012, 31 pages. Available online: http://static.bdbiosciences.com/documents/BD_Accuri_C6Flow_Cyto_Instrument_Manual.pdf.

* cited by examiner

METHODS FOR OPTICALLY ALIGNING LIGHT COLLECTION COMPONENTS AND OPTICALLY ALIGNED LIGHT COLLECTION SYSTEMS THEREOF

CROSS-REFERENCE TO RELATED APPLICATIONS

This application claims priority to U.S. Provisional Patent Application Ser. No. 62/090,248 filed Dec. 10, 2014, the disclosure of which application is incorporated herein by reference.

INTRODUCTION

In optical spectroscopy, a composition (e.g., a compound in a flow stream) is irradiated with light. To characterize the composition, light from the composition may be collected and directed to the active surface of a detector. Increasing the amount of light that reaches the detector increases the overall quality of optical signal. The amount of light that reaches the detector can be raised by increasing the surface area of the detector or by increasing collection of the light emitted by the sample using a lens or mirror.

Flow cytometry is a technique used to characterize and sort biological material, such as cells of a blood sample or particles of interest in any other type of biological or chemical sample. The technique may be used to record distributions or physically sort the biological material. A flow cytometer typically includes a sample reservoir for receiving a fluid sample, such as a blood sample, and a sheath reservoir containing a sheath fluid. The flow cytometer transports the particles (including cells) in the fluid sample as a cell stream to a flow cell, while also directing the sheath fluid to the flow cell. Within the flow cell, a liquid sheath is formed around the cell stream to impart a substantially uniform velocity on the cell stream. The flow cell hydrodynamically focuses the cells within the stream to pass through a laser at an interrogation point. As components of the flow stream move through the laser, light from the compounds in the flow stream are emitted and scattered. Variations in the materials, such as morphologies or fluorescent label, cause variations in the observed light which allow for characterization by collecting the light onto an optical detector.

SUMMARY

Aspects of the present disclosure include methods for optically aligning components of a light collection system. Methods according to certain embodiments include coupling one or more aligners and magnets positioned at the proximal end of a connector with one or more aligners and magnets positioned at the distal end of an optical adjustment component. In some embodiments, the aligners are protrusions (e.g., polygonal-shaped protrusions) and recesses (e.g., polygonal-shaped notches) and methods include inserting the protrusions into the recesses. In embodiments, methods also include contacting magnets positioned on the proximal end of the connector with magnets positioned on the distal end of the optical adjustment component. In certain embodiments, a flow cell nozzle is aligned with an optical adjustment component, such as a flow cell nozzle in a flow cytometer configured to propagate light emitted upstream from a flow stream through the distal end to the proximal end of the flow cell nozzle by total internal reflectance. In these embodiments, methods include coupling one or more aligners and magnets positioned at the proximal end of a flow cell nozzle with one or more aligners and magnets positioned at the distal end of an optical adjustment component.

Aspects of the disclosure also include optically aligned light collection systems. Systems according to certain embodiments include a connector having a first lens, one or more aligners and one or more magnets and an optical adjustment component having a second lens, one or more aligners and one or more magnets such that the connector lens is optically concentric with the lens of the optical adjustment component when the aligners and magnets of the connector are coupled to the aligners and magnets of the optical adjustment component. In some embodiments, the aligners are protrusions, grooves, notches or holes, such as a polygonal shaped protrusion or a polygonal shaped notch. In certain instances, the connector and the optical adjustment component each include three aligners and three magnets. In some instances, the magnets are disk shaped and the magnets of the connector are coupled to and concentric with the magnets of the optical adjustment component. In certain embodiments, the connector includes a flow cell nozzle, such as a flow cell nozzle in a flow cytometer configured to propagate light emitted by a sample in a flow stream upstream by total internal reflectance. In certain instances, the flow cell nozzles include a nozzle chamber having a proximal end and a distal end, a nozzle orifice positioned at the distal end of the nozzle chamber, a lens and one or more magnets and aligners positioned at the proximal end of the nozzle chamber. The connector may also include one or more fluid ports, such as a sample injection port and a sheath fluid port.

Aspects of the present disclosure also include systems for measuring light from a sample in a flow stream. In certain embodiments, systems include a light source, a detector and an optically aligned light collection system that includes: a flow cell having a nozzle chamber having a proximal end and a distal end, a nozzle orifice positioned at the distal end of the nozzle chamber, a lens and one or more aligners and magnets positioned at the proximal end of the nozzle chamber and an optical adjustment component having a lens and one or more aligners and magnets positioned at the distal end of the optical adjustment component. In some embodiments, the system is a flow cytometer. In some instances, the optical adjustment component is non-releasably integrated into the flow cytometer. The optical adjustment component may include one or more of a focusing lens, a magnifying lens, a de-magnifying lens and collimating lens. The optical adjustment component may also include a wavelength separator, such as a cutoff filter. In embodiments, the detector may be positioned orthogonal to the axis of the flow stream.

Aspects of the disclosure also include methods for irradiating a sample in a flow stream in an interrogation field with a light source, detecting light emitted by the sample in the flow stream by the subject optically aligned light collection systems and measuring the detected light at one or more wavelengths. In some instances, the light detected from the sample in the flow stream is propagated upstream through a flow cell nozzle orifice by total internal reflectance. In certain embodiments, light is collected and collimated or spatially separated light through one or more of the subject optically aligned light collection systems.

BRIEF DESCRIPTION OF THE FIGURES

The invention may be best understood from the following detailed description when read in conjunction with the accompanying drawings. Included in the drawings are the following figures.

DETAILED DESCRIPTION

Figure 1B:
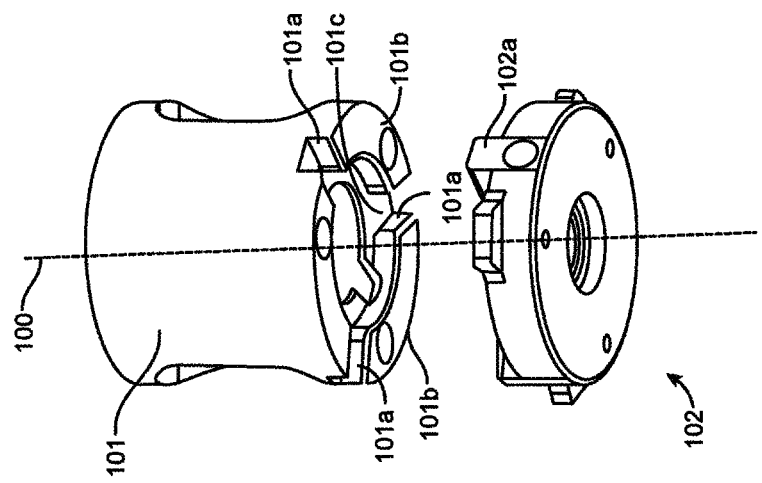
FIG. 1B illustrates a bottom-perspective view optically aligning components of a light collection system according to certain embodiments.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the present disclosure provides systems for optically aligning releasably attachable components. In further describing embodiments of the disclosure, methods for aligning a components of a light collection system are first described in greater detail. Next, light collection systems optically aligned by the subject methods are described. Systems and methods for measuring light emitted by a sample (e.g., in a flow stream) are described are also provided.

Methods for Optically Aligning Components of a Light Collection System

Aspects of the disclosure include methods for optically aligning components of a light collection system. In some embodiments, the subject methods include optically aligning an optical adjustment component with a flow cell nozzle, such as a flow cell nozzle in a flow cytometer configured to propagate light emitted upstream from a flow stream through the distal end to the proximal end of the flow cell nozzle by total internal reflectance. The phrase "optically aligning" is used herein its conventional sense to refer to positioning two or more optical components in line with each other such that the components are optically concentric (i.e., have the same optical axis). For example, methods include positioning two or more light collection components such that the optical axis of each component is displaced from each other by 100 µm or less when measured orthogonally to the optical axis, such as 50 µm or less, such as 25 µm or less, such as 15 µm or less, such as 10 µm or less, such as 5 µm or less, such 2 µm or less, such as 1 µm or less, such as 0.5 µm or less, such as 0.1 µm or less, such as 0.05 µm or less, such as 0.01 µm or less, such as 0.005 µm or less and including where the optical center of each component is displaced from each other by 0.001 µm or less when measured orthogonally to the optical axis. In embodiments, after alignment by the subject methods the optical center of a first light collection component is displaced from the optical center of a second light collection component by 100 µm or less when measured orthogonally to the optical axis, such as 50 µm or less, such as 25 µm or less, such as 15 µm or less, such as 10 µm or less, such as 5 µm or less, such 2 µm or less, such as 1 µm or less, such as 0.5 µm or less, such as 0.1 µm or less, such as 0.05 µm or less, such as 0.01 µm or less, such as 0.005 µm or less and including by 0.001 µm or less when measured orthogonally to the optical axis.

As discussed in greater detail below, light collection systems optically aligned by the subject methods include a connector component and an optical adjustment component. The connector component includes one or more first lenses, one or more aligners and one or more magnets. Likewise, the optical adjustment component includes one or more lenses, one or more aligners and one or more magnets. In embodiments, the connector lens is optically concentric with the lens of the optical adjustment component when the aligners and magnets of the connector are coupled to the aligners and the magnets of the optical adjustment component. In embodiments, the connector component has a proximal end and distal end where light from the distal end is propagated through one or more lenses to the proximal end of the connector. The length (as measured from the proximal to the distal end) of the connector may vary ranging from 5 mm to 100 mm, such as from 6 mm to 90 mm, such as from 7 mm to 80 mm, such as from 8 mm to 70 mm, such as from 9 mm to 60 mm and including from 10 mm to 50 mm. In some embodiments, the connector is cylindrical and has a length (as measured along the longitudinal axis) ranging from 5 mm to 100 mm, such as from 7 mm to 90 mm, such as from 10 mm to 80 mm, such as from 12 mm to 70 mm, such as from 15 mm to 60 mm and including from 25 mm to 50 mm. Depending on the diameter of the lens in the connector, the connector may have a width which varies, ranging from 5 mm to 50 mm, such as from 6 mm to 45 mm, such as from 7 mm to 40 mm, such as from 8 mm to 35 mm, such as from 9 mm to 30 mm and including from 10 mm to 25 mm. For example, where the connector is cylindrical, the diameter of the connector may be from 5 mm to 50 mm, such as from 6 mm to 45 mm, such as from 7 mm to 40 mm, such as from 8 mm to 35 mm, such as from 9 mm to 30 mm and including from 10 mm to 25 mm. The length (as measured from the proximal to the distal end) of the optical adjustment component may vary ranging from 5 mm to 100 mm, such as from 6 mm to 90 mm, such as from 7 mm to 80 mm, such as from 8 mm to 70 mm, such as from 9 mm to 60 mm and including from 10 mm to 50 mm. In some embodiments, the optical adjustment component is cylindrical and has a length (as measured along the longitudinal axis ranging from 5 mm to 100 mm, such as from 7 mm to 90 mm, such as from 10 mm to 80 mm, such as from 12 mm to 70 mm, such as from 15 mm to 60 mm and including from 25 mm to 50 mm. Depending on the diameter of the lens in the optical adjustment component, the optical adjustment component may have a width which varies, ranging from 5 mm to 50 mm, such as from 6 mm to 45 mm, such as from 7 mm to 40 mm, such as from 8 mm to 35 mm, such as from 9 mm to 30 mm and including from 10 mm to 25 mm. For example, where the optical adjustment component is cylindrical, the diameter of the connector may be from 5 mm to 50 mm, such as from 6 mm to 45 mm, such as from 7 mm to 40 mm, such as from 8 mm to 35 mm, such as from 9 mm to 30 mm and including from 10 mm to 25 mm.

In practicing the subject methods according to certain embodiments, a connector is aligned with an optical adjustment component by coupling one or more aligners positioned at the proximal end of the connector to one or more aligners positioned at the distal end of the optical adjustment component. By "coupling" is meant that the aligners at the proximal end of the connector are brought into contact (e.g., press-fitted) with the aligners positioned at the distal end of the optical adjustment component. For example, where an aligner at the proximal end of the connector is an alignment protrusion, and the aligner at the distal end of the optical adjustment component is an alignment recess, methods may include inserting the protrusion of the connector into the recess of the optical adjustment component such that the outer surfaces of the protrusion are spaced apart from the inner walls of the recess by 100 μm or less, such as 50 μm or less, such as 25 μm or less, such as 15 μm or less, such as 10 μm or less, such as 5 μm or less, such 2 μm or less, such as 1 μm or less, such as 0.5 μm or less, such as 0.1 μm or less, such as 0.05 μm or less, such as 0.01 μm or less, such as 0.005 μm or less and including by 0.001 μm. In certain instances, methods include inserting the protrusion of the connector into the recess of the optical adjustment component such that the outer surfaces of the protrusion are in contact the inner walls of the recess. In some embodiments, methods include inserting the protrusion into the recess such that the top surface of the protrusion is spaced apart from the bottom wall of the recess by 100 μm or less, such as 50 μm or less, such as 25 μm or less, such as 15 μm or less, such as 10 μm or less, such as 5 μm or less, such 2 μm or less, such as 1 μm or less, such as 0.5 μm or less, such as 0.1 μm or less, such as 0.05 μm or less, such as 0.01 μm or less, such as 0.005 μm or less and including by 0.001 μm or less. In certain instances, the protrusion is inserted into the recess such that the top surface of the protrusion is in contact with the bottom wall of the recess and the outer side surfaces of the protrusion are in contact with the inner walls of the recess.

As described in greater detail below, the connector and optical adjustment component may include any number of aligners, such as 2 or more aligners, such as 3 or more aligners, such as 4 or more aligners, such as 5 or more aligners, such as 7 or more aligners and including 10 or more aligners. In embodiments, each aligner on the connector is coupled to a complimentary aligner on the optical adjustment component. Accordingly, optically aligning the connector and optical adjustment component may include coupling 2 or more aligners together, such as 3 or more aligners, such as 4 or more aligners, such as 5 or more aligners and including coupling 10 or more aligners together.

Depending on the type of aligner on the proximal end of the connector and the distal end of the optical adjustment component, coupling the connector to the optical adjustment component may vary. In some embodiments, the proximal end of the connector includes one or more alignment protrusions (e.g., 3 or more polygonal-shaped protrusions) and the distal end of the optical component includes one or more alignment recesses (e.g., 3 or more polygonal-shaped notches). In these embodiments, coupling the proximal end of the connector to the distal end of the optical adjustment component includes inserting each of the alignment protrusions of the connector into the alignment recesses of the optical adjustment component.

In certain embodiments, the connector and optical adjustment component are cylindrical and each of the aligners is identical and spaced equidistant from each other on the connector and the optical adjustment component such that the connector proximal end and the optical adjustment component distal end are rotationally symmetrical about the optical axis. In other words, the connector and the optical adjustment component in these embodiments are non-orientation specific and may be coupled together in a plurality of different orientations. For example, the connector proximal end and optical adjustment distal end may include 3 or more (such as 4 or more and including 5 or more) identical and equidistant spaced aligners such that the connector and optical adjustment component may be coupled together in 3 or more (such as 4 or more and including 5 or more) different rotational orientations.

In other embodiments, both the proximal end of the connector and the distal end of the optical adjustment component include one or more alignment protrusions and one or more alignment recesses. In these embodiments, coupling the proximal end of the connector to the distal end of the optical adjustment component includes inserting the alignment protrusions of the connector into the alignment recesses in the optical adjustment component and inserting the alignment protrusions of the optical adjustment component into the alignment recesses of the connector.

As discussed below, the length of each alignment protrusion may vary ranging from 1 mm to 50 mm, such as from 2 mm to 45 mm, such as from 3 mm to 40 mm, such as from 4 m to 35 mm, such as from 5 mm to 30 mm and including from 10 mm to 20 mm. Likewise, the depth of each alignment recess may vary ranging from 1 mm to 50 mm, such as from 2 mm to 45 mm, such as from 3 mm to 40 mm, such as from 4 mm to 35 mm, such as from 5 mm to 30 mm and including from 10 mm to 20 mm. In coupling the connector to the optical adjustment component according to certain embodiments, each alignment protrusion is inserted to the full depth of the alignment recess such that proximal end of the connector is separated from distal end of the optical adjustment component by 100 µm or less, such as 50 µm or less, such as 25 µm or less, such as 15 µm or less, such as 10 µm or less, such as 5 µm or less, such 2 µm or less, such as 1 µm or less, such as 0.5 µm or less, such as 0.1 µm or less, such as 0.05 µm or less, such as 0.01 µm or less, such as 0.005 µm or less and including by 0.001 µm or less. In certain instances, coupling the connector to the optical adjustment component includes bringing the top surface of each alignment protrusion into contact with the bottom wall of each alignment recess such that the proximal end of the connector is in physical contact with the distal end of the optical adjustment component.

Where the length of the alignment protrusion is greater than the depth of the alignment recess, when coupled together the proximal end of the connector may be spaced apart from the distal end of the optical adjustment component by 1 mm or more, such as 2 mm or more, such as 3 mm or more, such as 5 mm or more and including by 10 mm or more.

In embodiments, the connector is also aligned with the optical adjustment component by coupling one or more magnets positioned at the proximal end of the connector to one or more magnets positioned at the distal end of the optical adjustment component. The term "magnet" is used herein in its conventional sense to refer to a magnetic material that has a persistent magnetic field such that the magnetic field from the magnet does not substantially decrease over time. For example, the magnet may be an iron alloy material having aluminum, nickel and colbalt (i.e., Alnico magnets), a ceramic or ferrite magnet, a rare-earth magnet such as samarium-cobalt magnets (e.g., $SmCo_5$), neodymium alloy (NdFeB) magnets (e.g., $Nd_2Fe_{14}B$) or a combination thereof. Depending on the size of the magnet, the magnet field produced by magnets of interest positioned at the connector proximal end range from 0.01 T to 10 T, or from 0.01 T to 5 T, or from 0.01 T to 2 T, or from 0.1 T to 2 T, or from 0.1 T to 1.5 T, including from 0.1 T to 1 T.

In embodiments, the magnets at the proximal end of the connector are placed into physical contact with the magnets positioned at the distal end of the optical adjustment component. In certain embodiments, the magnets positioned at the proximal end of the connector and the distal end of the optical adjustment component are disk shaped and alignment of the connector and the optical adjustment component is achieved when each magnet of the connector is concentric (i.e., centered) with each coupled magnet of the optical adjustment component. For example, in certain instances the connector and the optical adjustment component are optically aligned when the center of each magnet on connector is displaced from the center of each coupled magnet on the optical adjustment component by 100 µm or less, such as 50 µm or less, such as 25 µm or less, such as 15 µm or less, such as 10 µm or less, such as 5 µm or less, such 2 µm or less, such as 1 µm or less, such as 0.5 µm or less, such as 0.1 µm or less, such as 0.05 µm or less, such as 0.01 µm or less, such as 0.005 µm or less and including by 0.001 µm or less.

By placing the magnets of the connector into contact with the magnets of the optical adjustment component, the connector is aligned and releasably attached to the optical adjustment component by the magnetic attraction between each set of magnet contacts. In some embodiments, coupling of the magnets of the connector to the magnets of the optical adjustment component maintains optical alignment of the connector and the optical adjustment component for a period of time, as desired, such as until the connector is deliberately and physically detached from the optical adjustment component. For example, coupling of the magnets of the connector to the magnets of the optical adjustment component maintains optical alignment of the connector and the optical adjustment component for 1 hour or longer, such as 4 hours or longer, such as 6 hours or longer, such as 12 hours or longer, such as 18 hours or longer, such as 24 hours or longer, such as 3 days or longer, such as 7 days or longer, such as 2 weeks or longer and including for 1 month or longer.

As described in greater detail below, the connector and optical adjustment component may include any number of magnets, such as 2 or more magnets, such as 3 or more magnets, such as 4 or more magnets, such as 5 or more magnets, such as 7 or more magnets and including 10 or more magnets. In embodiments, each magnet on the connector is coupled to a magnet on the optical adjustment component. Accordingly, aligning the connector and optical adjustment component may include coupling 2 or more magnets together, such as 3 or more magnets, such as 4 or more magnets, such as 5 or more magnets and including coupling 10 or more magnets together.

In certain embodiments, the connector and optical adjustment component are cylindrical and each of the magnets are identical and spaced equidistant from each other on the connector proximal end and the optical adjustment component distal end such that the connector and the optical adjustment component are rotationally symmetrical about the optical axis. In other words, the connector and the optical adjustment component in these embodiments are non-orientation specific and may be coupled together in a plurality of different orientations. For example, the connector proximal end and optical adjustment distal end may include 3 or more (such as 4 or more and including 5 or more) identical and equidistant spaced magnets such that the connector and optical adjustment component may be coupled together in 3 or more (such as 4 or more and including 5 or more) different rotational orientations.

Figure 1A:
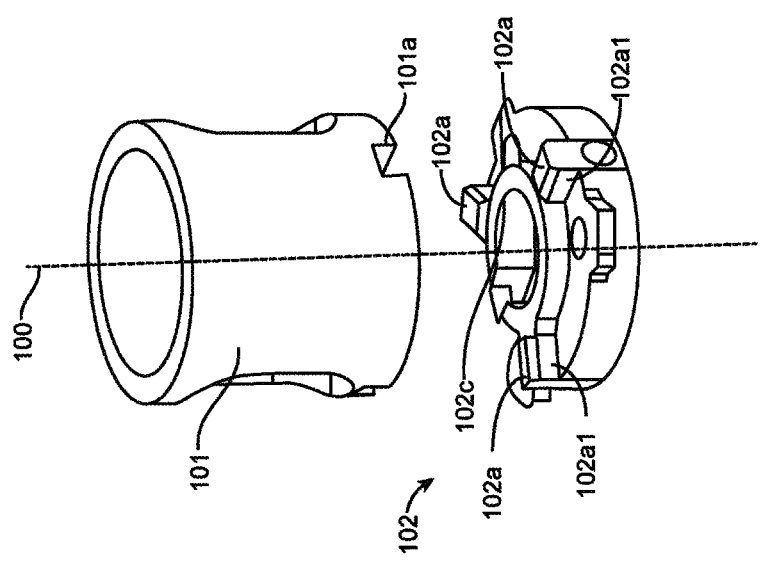
FIG. 1A illustrates a top-perspective view optically aligning components of a light collection system according to certain embodiments.

FIGS. 1A and 1B illustrate optically aligning components of a light collection system according to certain embodiments. FIG. 1A depicts a top-perspective view and FIG. 1B depicts a bottom-perspective view of optical adjustment component 101 having alignment recesses 101a and magnets 101b and connector component 102 having alignment protrusions 102a and magnets 102b. Alignment protrusions 102a each have a top surface and side surfaces 102a1 which in some embodiments contacts the inner walls of alignment recesses 101a on optical adjustment component 101. As discussed above, when alignment recesses 101a and magnets 101b at the distal end of the optical adjustment component are coupled with alignment protrusions 102a and 102b at the proximal end of the connector, respectively, the lens of optical adjustment component 101 and connector 102 are optically concentric illustrated by common optical axis 100. Coupling of optical adjustment component 101 to connector 102 brings surface 101c at the distal of optical adjustment component 101 into contact with surface 102c at the proximal end of the connector.

In certain embodiments, methods include optically aligning a flow cell nozzle with the optical adjustment component, such as a flow cell nozzle in a flow cytometer configured to propagate light emitted upstream from a flow stream through the distal end to the proximal end of the flow cell nozzle by total internal reflectance. In these embodiments, the flow cell may be releasably attached to the connector, such as with an adhesive. In other embodiments, the flow cell nozzle is co-molded with the connector. In yet other embodiments, the connector is integrated into the proximal end of the flow cell nozzle. In still other embodiments, the connector is entirely replaced by a flow cell nozzle and the proximal end of the flow cell nozzle is directly coupled to the optical adjustment component. In these embodiments, methods include coupling one or more aligners and magnets positioned at the proximal end of the flow cell nozzle with one or more aligners and magnets positioned at the distal end of an optical adjustment component, as described above. In certain instances, the optical adjustment component is fixed inside of the flow cytometer and methods include optically aligning the flow cell nozzle with the optical adjustment component in the flow cytometer by coupling aligners and magnets at the proximal end of the flow cell nozzle to aligners and magnets at the distal end of the optical adjustment component in the flow cytometer.

In certain embodiments, methods include separating the connector from the optical adjustment component. By "separating" is meant that the connector is not in any physical contact with the optical adjustment component, including where each of the aligners of the connector are removed from contact with the aligners of the optical adjustment component and where each of the magnets of the connector are removed from contact with the magnets of the optical adjustment component.

Optically Aligned Light Collection Systems

As summarized above, aspects of the present disclosure also include optically aligned light collection systems configured for collecting light emitted by a sample (e.g., in a flow stream of a flow cytometer). In some embodiments, the subject systems include an optical adjustment component optically aligned with a flow cell nozzle, such as a flow cell nozzle in a flow cytometer configured to propagate light emitted upstream from a flow stream through the distal end to the proximal end of the flow cell nozzle by total internal reflectance. As discussed above, by optically aligned is meant that two or more optical components are positioned in line with each other such that the components are optically concentric. For example, optically aligned light collection systems include two or more components where the optical center of each component is displaced from each other by 100 µm or less when measured orthogonally to the optical axis, such as 50 µm or less, such as 25 µm or less, such as 15 µm or less, such as 10 µm or less, such as 5 µm or less, such 2 µm or less, such as 1 µm or less, such as 0.5 µm or less, such as 0.1 µm or less, such as 0.05 µm or less, such as 0.01 µm or less, such as 0.005 µm or less and including where the optical center of each component is displaced from each other by 0.001 µm or less when measured orthogonally to the optical axis. In embodiments, light passing through the center of a first optical component in systems of interest is displaced from the center of a second optical component by 100 µm or less when measured orthogonally to the optical axis, such as 50 µm or less, such as 25 µm or less, such as 15 µm or less, such as 10 µm or less, such as 5 µm or less, such 2 µm or less, such as 1 µm or less, such as 0.5 µm or less, such as 0.1 µm or less, such as 0.05 µm or less, such as 0.01 µm or less, such as 0.005 µm or less and including where the center of each optical component is displaced from each other by 0.001 µm or less when measured orthogonally to the optical axis.

In embodiments, optically aligned light collection systems include a connector component and an optical adjustment component. The connector includes a first lens, one or more aligners and one or more magnets. The optical adjustment component includes a second lens, one or more aligners and one or more magnets. In embodiments, the connector lens is optically concentric with the lens of the optical adjustment component when the aligners and magnets of the connector are coupled to the aligners and magnets of the optical adjustment component. The connector has a proximal end and distal end and is coupled to the optical adjustment component at the proximal end. The length (as measured from the proximal to the distal end) may vary ranging from 5 mm to 100 mm, such as from 6 mm to 90 mm, such as from 7 mm to 80 mm, such as from 8 mm to 70 mm, such as from 9 mm to 60 mm and including from 10 mm to 50 mm. In some embodiments, the connector component is cylindrical and has a length (as measured along the longitudinal axis ranging from 5 mm to 100 mm, such as from 7 mm to 90 mm, such as from 10 mm to 80 mm, such as from 12 mm to 70 mm, such as from 15 mm to 60 mm and including from 25 mm to 50 mm. The width of the connector may also vary, ranging from 5 mm to 50 mm, such as from 6 mm to 45 mm, such as from 7 mm to 40 mm, such as from 8 mm to 35 mm, such as from 9 mm to 30 mm and including from 10 mm to 25 mm. For example, where the connector is cylindrical, the diameter of the connector may be from 5 mm to 50 mm, such as from 6 mm to 45 mm, such as from 7 mm to 40 mm, such as from 8 mm to 35 mm, such as from 9 mm to 30 mm and including from 10 mm to 25 mm.

The connector includes one or more aligners positioned at the proximal end of connector. The connector may include any number of aligners, so long as coupling of the aligners and magnets (discussed below) on the connector to the aligners and magnets on the optical adjustment component is sufficient to position and maintain optical concentricity of the connector lens and the lens of the optical adjustment component. For example, connectors of interest may include 2 or more aligners, such as 3 or more aligners, such as 4 or more aligners, such as 5 or more aligners, such as 7 or more aligners and including 10 or more aligners. Any suitable type of aligner may be employed, such as an alignment protrusion, an alignment rail, an alignment notch, an alignment groove, an alignment slot, an alignment hole or a combination thereof. For example, in some instances the connector proximal end includes one or more protrusions. In other instances, the connector proximal end includes one or more notches. In certain instances, the connector proximal end includes one or more protrusions and one or more notches.

The shape of aligners positioned at the proximal end of the connector may vary, where cross-sectional shapes of interest include, but are not limited to rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. In some embodiments, the aligners are cylindrically shaped. In other embodiments, the aligners are spherical. In yet other embodiments, the aligners are polygonal-shaped, such as square-shaped or rectangular.

The width of each aligner may vary ranging from 1 mm to 25 mm, such as from 2 mm to 22 mm, such as from 3 mm to 20 mm, such as from 4 mm to 17 mm and including from 5 mm to 15 mm. The length of each aligner positioned at the proximal end of the connector ranges from 1 mm to 50 mm, such as from 2 mm to 45 mm, such as from 3 mm to 40 mm, such as from 4 m to 35 mm, such as from 5 mm to 30 mm and including from 10 mm to 20 mm. Where the aligner positioned at the proximal end of the connector is an alignment recess, such as a notch, a slot, a groove or a hole, the depth of the aligner may range from 1 mm to 50 mm, such as from 2 mm to 45 mm, such as from 3 mm to 40 mm, such as from 4 m to 35 mm, such as from 5 mm to 30 mm and including from 10 mm to 20 mm.

The aligners may be positioned at any location on the proximal end of the connector. For example, in some embodiments one or more aligners are positioned adjacent to outer edge of the lens of the connector, such as 1 mm or more from the lens of the connector, such as 2 mm or more, such as 3 mm or more, such as 4 mm or more and including 5 mm or more from the outer edge of the lens of the connector. In other embodiments, one or more aligners are positioned along the outer edge of the connector proximal end. In still other embodiments, one or more aligners are positioned between the outer edge of the connector proximal end and the outer edge of the lens of the connector, such as 1 mm or more from the outer edge of the connector proximal end, such as 2 mm or more, such as 3 mm or more, such as 4 mm or more and including 5 mm or more from the outer edge of the connector proximal end.

Where the connector includes more than one aligner, the distance between each aligner may vary, being spaced apart by 2 mm or more, such as by 3 mm or more, such as by 5 mm or more, such as by 7 mm or more, such as by 10 mm or more and including by 25 mm or more. Where the connector includes three or more aligners, the distance between each aligner may be the same or different or a combination thereof. In some embodiments, the distance between each aligner is different. In other embodiments, each aligner is spaced equidistant from each other. In certain embodiments, the connector includes 3 aligners that are equidistantly spaced along the outer edge of the connector proximal end. For instance, the connector may include 3 polygonal-shaped (e.g., square or rectangular) protrusions (e.g., complimentary to 3-polygonal-shaped recesses in the optical adjustment component) which are spaced equidistantly from each other along the outer edge of the connector proximal end.

As discussed above, the top and side surfaces of each aligner may contact the aligner surfaces of the optical adjustment component. In some embodiments, the surfaces of the aligners at the proximal end of the connector are substantially flat, such as to maximize contact between the aligners of the optical adjustment component. By "substantially flat" is meant that the walls of the aligner exhibit little to no deviation along its surface, such as where crevices or protrusions along the aligner walls are 100 μm or less as measured from the wall surface, such as 50 μm or less, such as 25 μm or less, such as 15 μm or less, such as 10 μm or less, such as 5 μm or less, such 2 μm or less, such as 1 μm or less, such as 0.5 μm or less, such as 0.1 μm or less, such as 0.05 μm or less, such as 0.01 μm or less, such as 0.005 μm or less and including by 0.001 μm or less as measured from the wall surface. For example, where the connector proximal end includes one or more protrusions, the outer walls (i.e., top and side surfaces) of the protrusions are substantially flat to maximize contact with the inner walls of recesses (e.g., bottom and side walls) in the optical adjustment component distal end.

Where the length of the alignment protrusion is the same as the depth of the alignment recess, when coupled together the proximal end of the connector may be in physical contact with distal end of the optical adjustment component. Where the length of the alignment protrusion is greater than the depth of the alignment recess, when coupled together the proximal end of the connector may be spaced apart from the distal end of the optical adjustment component by 1 mm or more, such as 2 mm or more, such as 3 mm or more, such as 5 mm or more and including by 10 mm or more.

The proximal end of the connector also includes one or more magnets. As discussed above, each magnet is a magnetic material that has a persistent magnetic field such that the magnetic field from the magnet does not substantially decrease over time. For example, the magnet may be an iron alloy material having aluminum, nickel and colbalt (i.e., Alnico magnets), a ceramic or ferrite magnet, a rare-earth magnet such as samarium-cobalt magnets (e.g., $SmCo_5$), neodymium alloy (NdFeB) magnets (e.g., $Nd_2Fe_{14}B$), among other types of magnets or a combination thereof. Depending on the size of the magnet, the magnet field produced by magnets of interest positioned at the connector proximal end range from 0.01 T to 10 T, or from 0.01 T to 5 T, or from 0.01 T to 2 T, or from 0.1 T to 2 T, or from 0.1 T to 1.5 T, including from 0.1 T to 1 T. The connector may include any number of magnets, so long as coupling of the magnets on the connector to the magnets on the optical adjustment component is sufficient to maintain optical concentricity of the connector lens with lens of the optical adjustment component. For example, the proximal end of the connector may include 2 or more magnets, such as 3 or more magnets, such as 4 or more magnets, such as 5 or more magnets, such as 7 or more magnets and including 10 or more magnets.

The shape of the magnets positioned at the proximal end of the connector may vary, where cross-sectional shapes of interest include, but are not limited to rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. In some embodiments, magnets of interest are cylindrically shaped. In other embodiments, the magnets are disk-shaped. In yet other embodiments, the magnets are square-shaped. In still other embodiments, the magnets are rectangular.

The width of each magnet may vary ranging from 1 mm to 25 mm, such as from 2 mm to 22 mm, such as from 3 mm to 20 mm, such as from 4 mm to 17 mm and including from 5 mm to 15 mm. The thickness of each magnet ranges from 0.01 mm to 10 mm, such as from 0.05 mm to 9 mm, such as from 0.1 mm to 8 mm, such as from 0.5 mm to 7 mm, such as from 1 mm to 6 mm and including from 2 mm to 5 mm. In certain embodiments, magnets positioned at the proximal end of the connector are disk-shaped. In these embodiments, the disk-shaped magnets have a diameter ranging from 1 mm to 25 mm, such as from 2 mm to 22 mm, such as from 3 mm to 20 mm, such as from 4 mm to 17 mm and including from 5 mm to 15 mm and a thickness ranging from 0.01 mm to 10 mm, such as from 0.05 mm to 9 mm, such as from 0.1 mm to 8 mm, such as from 0.5 mm to 7 mm, such as from 1 mm to 6 mm and including from 2 mm to 5 mm.

The magnets may be positioned at any location on the proximal end of the connector. For example, in some embodiments one or more magnets are positioned adjacent to the aligner, such as 1 mm or more from the lens of the connector, such as 2 mm or more, such as 3 mm or more, such as 4 mm or more and including 5 mm or more from aligner. In other embodiments, one or more magnets are positioned adjacent to outer edge of the lens of the connector, such as 1 mm or more from the lens of the connector, such as 2 mm or more, such as 3 mm or more, such as 4 mm or more and including 5 mm or more from the outer edge of the lens of the connector. In other embodiments, one or more magnets are positioned along the outer edge of the connector proximal end. In still other embodiments, one or more magnets are positioned between the outer edge of the connector proximal end and the outer edge of the lens of the connector, such as 1 mm or more from the outer edge of the connector proximal end, such as 2 mm or more, such as 3 mm or more, such as 4 mm or more and including 5 mm or more from the outer edge of the connector proximal end.

Where the proximal end of the connector includes more than one magnet, the distance between each magnet may vary, such as where the magnets are spaced apart by 2 mm or more, such as by 3 mm or more, such as by 5 mm or more, such as by 7 mm or more, such as by 10 mm or more and including by 25 mm or more. Where the connector includes three or more magnets, the distance between each magnet may be the same or different or a combination thereof. In some embodiments, the distance between each magnet is different. In other embodiments, the magnets are spaced equidistant from each other. In certain embodiments, the connector includes 3 magnets that are equidistantly spaced along the outer edge of the connector proximal end. For instance, the connector may include 3 disk-shaped magnets which are spaced equidistantly from each other along the outer edge of the connector proximal end.

As described in greater detail below, the top surface of magnets positioned at the connector proximal end contact the top surface of magnets positioned at the distal end of the optical adjustment component. In some embodiments, the top surface of the magnets is substantially flat to maximize contact between the magnets of the connector and the magnets of the optical adjustment component. In these embodiments, the top surface of the magnets exhibits little to no deviation along its surface, such as where crevices or protrusions along the magnet top surface are 100 µm or less as measured from the top surface, such as 50 µm or less, such as 25 µm or less, such as 15 µm or less, such as 10 µm or less, such as 5 µm or less, such 2 µm or less, such as 1 µm or less, such as 0.5 µm or less, such as 0.1 µm or less, such as 0.05 µm or less, such as 0.01 µm or less, such as 0.005 µm or less and including by 0.001 µm or less as measured from top surface.

Figure 2:
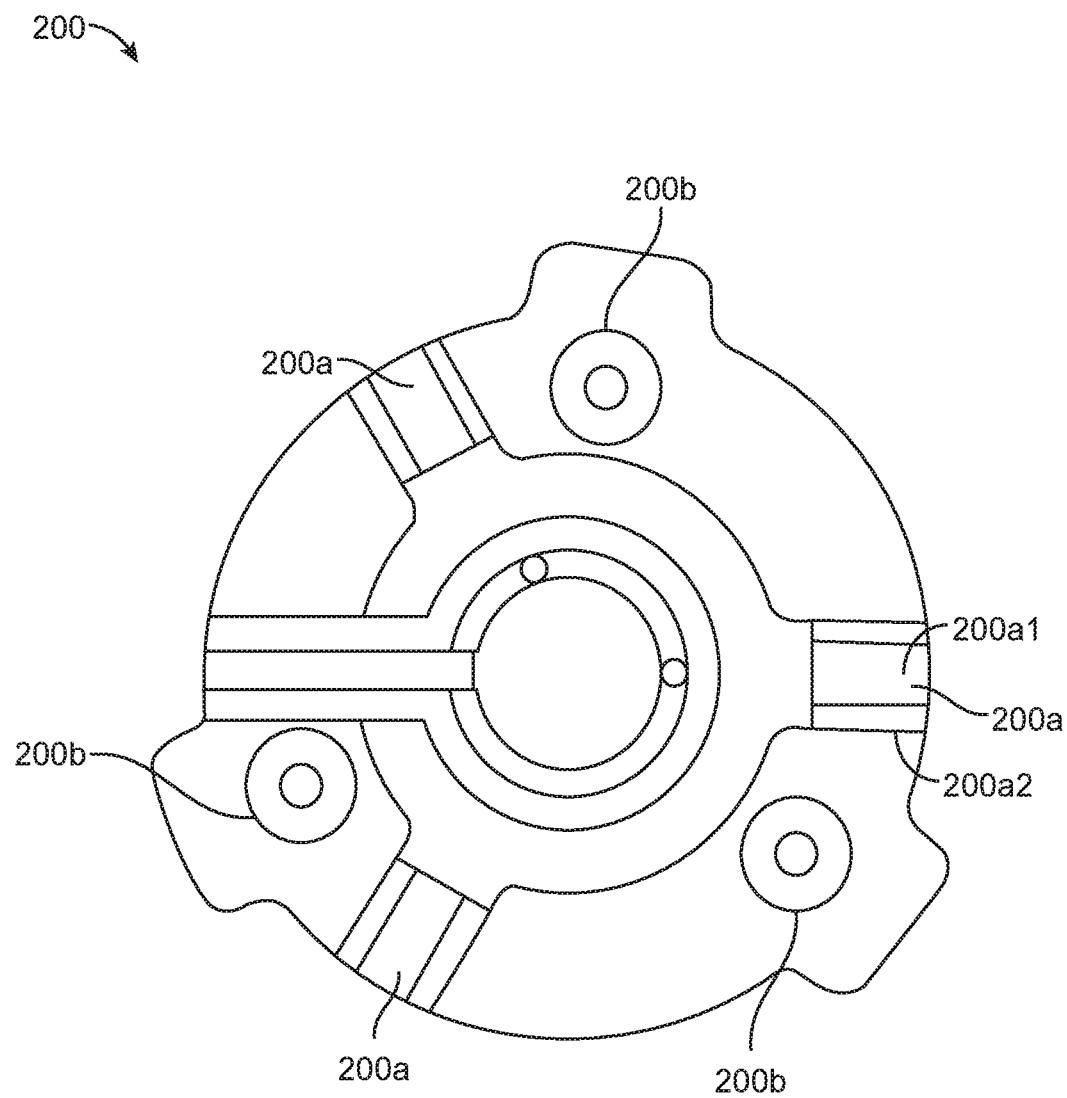
FIG. 2 depicts a top-view of the proximal end of a connector according to certain embodiments.

FIG. 2 depicts a top-view of the proximal end of a connector according to certain embodiments. Connector 200 includes three aligners 200a and three magnets 200b. Aligners 200a are polygonal shaped protrusions extending from the connector proximal end and are positioned along the outer edge at equal distances from each other. Each aligner 200a includes a top surface 200a1 and side surfaces 200a2 which contact the walls when positioned in an alignment notch of an optical adjustment component (as described in greater detail below).

As summarized above, the connector includes one or more lenses that are optically concentric with the lens on the optical adjustment component when an aligner and magnet on the connector are coupled to an aligner and magnet on the optical adjustment component. In embodiments, the connector lens may be a collimating lens, a focusing lens, a magnifying lens, a de-magnifying lens, or some other lens. Depending on the size of the connector, the width of the lens may vary, ranging from 5 mm to 50 mm, such as from 6 mm to 45 mm, such as from 7 mm to 40 mm, such as from 8 mm to 35 mm, such as from 9 mm to 30 mm and including from 10 mm to 25 mm. The numerical aperture of the lens may also vary, ranging from 0.01 to 2.0, such as from 0.05 to 1.9, such as from 0.1 to 1.8, such as from 0.2 to 1.7, such as from 0.3 to 1.6, and including a numerical aperture ranging from 0.5 to 1.5. Likewise, the focal length of the lens varies, ranging from 0.1 mm to 20 mm, such as from 0.5 mm to 19 mm, such as from 1 mm to 18 mm and including from 2 mm to 15 mm.

In some embodiments, the connector includes a focusing lens having a magnification ratio from 0.1 to 0.95, such as a magnification ratio of from 0.2 to 0.9, such as a magnification ratio of from 0.3 to 0.85, such as a magnification ratio of from 0.35 to 0.8, such as a magnification ratio of from 0.5 to 0.75 and including a magnification ratio of from 0.55 to 0.7, for example a magnification ratio of 0.6. In other embodiments, the connector includes one or more collimating lenses. For example, the connector in certain instances includes a single collimating lens. In other instances, the connector includes two collimating lenses.

In some cases, the lens is releasably attached to the connector. The term "releasably" is used herein in its conventional sense to mean that the one or more lenses in the connector may be freely detached and re-attached to the connector. Where the lens is configured to be releasably attached to a connector, the connector may include one or more fasteners for attaching the lens to the connector. Suitable fasteners may include, but are not limited to, hook and loop fasteners, latches, notches, grooves, pins, tethers, hinges, Velcro, non-permanent adhesives or a combination thereof. In certain instances, the lens is screw threaded into the connector.

In certain embodiments, the connector includes one or more fluid ports, such as where the connector includes or is integrated into a flow cell nozzle and includes a sample injection port, a sheath fluid port or a combination thereof. In embodiments, the fluid port may be an orifice positioned in a wall of the connector, in the aligner or a combination thereof. Where the fluid port is an orifice positioned in a wall of the connector or in the aligner, the port orifice may be any suitable shape where cross-sectional shapes of interest include, but are not limited to: rectilinear cross sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion. In certain embodiments, the fluid port is a circular orifice. The size each fluid port orifice may vary depending on shape, in certain instances, having an opening ranging from 0.5 mm to 2.5 mm, such as from 0.75 mm to 2.25 mm, such as from 1 mm to 2 mm and including from 1.25 mm to 1.75 mm, for example 1.5 mm.

In some embodiments, the connector includes a flow cell nozzle, such as a flow cell nozzle in a flow cytometer configured to propagate light emitted upstream from a flow stream through the distal end to the proximal end of the flow cell nozzle by total internal reflectance. In some embodiments, the flow cell nozzle is releasably attached to the connector such as with an adhesive. In other embodiments, the flow cell nozzle is co-molded with the connector. In yet other embodiments, the connector is integrated with the flow cell nozzle. In still other embodiments, the connector is entirely replaced by a flow cell nozzle and the proximal end of the flow cell nozzle includes one or more aligners and one or more magnets for coupling to the optical adjustment component.

In certain embodiments, flow cell nozzles of interest are configured to propagate light in a flow cytometer that is emitted by a sample in a flow stream upstream by total internal reflectance. In these embodiments, the flow cell nozzles are configured to direct light propagated within the flow stream back into the flow cell nozzle through the nozzle orifice and collect the light with a lens positioned at the proximal end. The light collected is the light which is internally reflected within the flow stream. In some embodiments, the flow cell nozzle includes a nozzle chamber having a proximal end having a lens, one or more magnets and one or more aligners (as described above) and a distal end having a nozzle orifice in fluid communication with the flow stream of the flow cytometer. In some instances, flow cell nozzles of interest includes a proximal cylindrical portion defining a longitudinal axis and a distal frustoconical portion which terminates in a flat surface having the nozzle orifice that is transverse to the longitudinal axis. The length of the proximal cylindrical portion (as measured along the longitudinal axis) may vary ranging from 1 mm to 15 mm, such as from 1.5 mm to 12.5 mm, such as from 2 mm to 10 mm, such as from 3 mm to 9 mm and including from 4 mm to 8 mm. The length of the distal frustoconical portion (as measured along the longitudinal axis) may also vary, ranging from 1 mm to 10 mm, such as from 2 mm to 9 mm, such as from 3 mm to 8 mm and including from 4 mm to 7 mm. The diameter of the of the flow cell nozzle chamber may vary, in some embodiments, ranging from 1 mm to 10 mm, such as from 2 mm to 9 mm, such as from 3 mm to 8 mm and including from 4 mm to 7 mm.

In certain instances, the nozzle chamber is frustoconically shaped. In these embodiments, the length of the frustoconical nozzle chamber (as measured along the longitudinal axis transverse to the nozzle orifice), may range from 1 mm to 15 mm, such as from 1.5 mm to 12.5 mm, such as from 2 mm to 10 mm, such as from 3 mm to 9 mm and including from 4 mm to 8 mm. The diameter of the proximal portion of the frustoconical nozzle chamber may range from 1 mm to 10 mm, such as from 2 mm to 9 mm, such as from 3 mm to 8 mm and including from 4 mm to 7 mm.

Figure 4:
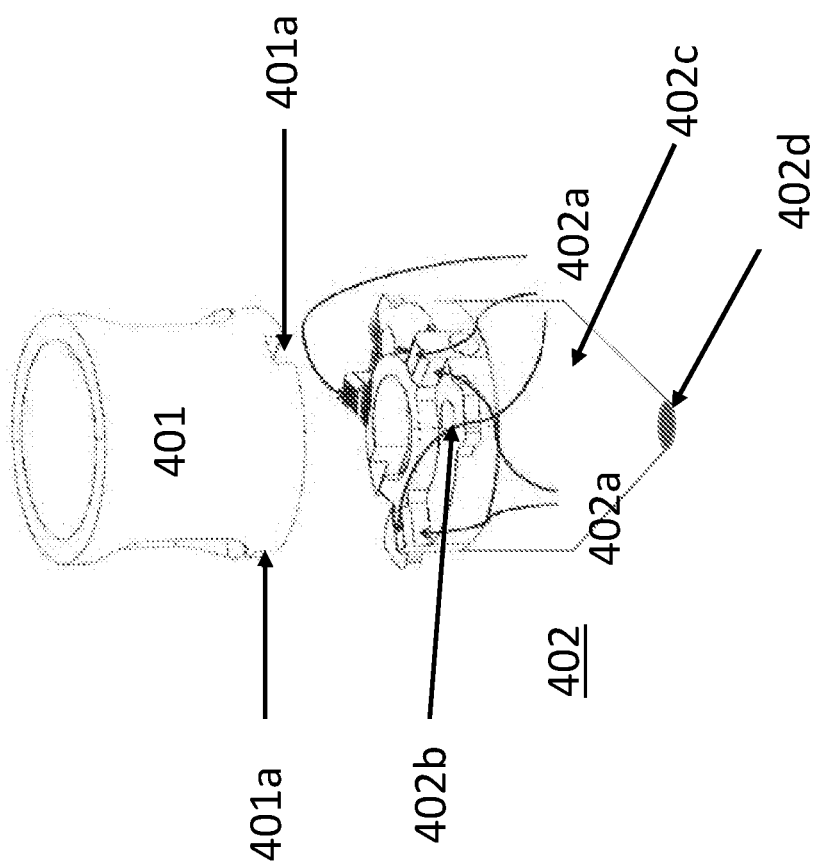
FIG. 4 depicts a top-perspective view of a flow cell nozzle and an optical adjustment component according to certain embodiments.

FIG. 4 illustrates optically aligning components of a light collection system according to certain embodiments. FIG. 4 depicts a top-perspective view of optical adjustment component 401 having alignment recesses 401a and flow cell nozzle 402 having alignment protrusions 402a and magnets 402b. Flow cell nozzle 402 includes a nozzle chamber 402c and a nozzle orifice 402d at the distal end of nozzle chamber 402c. Alignment protrusions 402a and magnets 402b are positioned at the proximal end of flow cell nozzle 402.

In certain embodiments, the flow cell nozzle includes one or more fluid ports, such as a sample injection port, a sheath fluid port or a combination thereof. In embodiments, the fluid port may be an orifice positioned in a wall of the nozzle chamber, in the aligner positioned on the proximal end of the flow cell nozzle or a combination thereof. The fluid port orifice may be any suitable shape where cross-sectional shapes of interest include, but are not limited to: rectilinear cross sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion. In certain embodiments, the fluid port is a circular orifice. The size each fluid port orifice may vary depending on shape, in certain instances, having an opening ranging from 0.5 mm to 2.5 mm, such as from 0.75 mm to 2.25 mm, such as from 1 mm to 2 mm and including from 1.25 mm to 1.75 mm, for example 1.5 mm. Depending on the desired characteristics of the flow stream in the flow cytometer, the fluid ports may be configured to convey fluid into the flow cell nozzle at a rate of 1 μL/sec or more, such as 2 μL/sec or more, such as 3 μL/sec or more, such as 5 μL/sec or more, such as 10 μL/sec or more, such as 15 μL/sec or more, such as 25 μL/sec or more, such as 50 μL/sec or more and including 100 μL/sec or more.

In certain embodiments, flow cell nozzles of interest for propagating light upstream by total internal reflectance include, but are not limited to those described in U.S. patent application Ser. No. 14/260,177 filed on Apr. 23, 2014, the disclosure of which is herein incorporated by reference.

As summarized above, the subject optically aligned light collection systems also include an optical adjustment component. In embodiments, the optical adjustment component includes one or more optical adjustment lenses, one or more aligners and one or more magnets. The length (as measured from the proximal to the distal end) of the optical adjustment component may vary ranging from 5 mm to 100 mm, such as from 6 mm to 90 mm, such as from 7 mm to 80 mm, such as from 8 mm to 70 mm, such as from 9 mm to 60 mm and including from 10 mm to 50 mm. In some embodiments, the optical adjustment component is cylindrical and has a length (as measured along the longitudinal axis ranging from 5 mm to 100 mm, such as from 7 mm to 90 mm, such as from 10 mm to 80 mm, such as from 12 mm to 70 mm, such as from 15 mm to 60 mm and including from 25 mm to 50 mm. Depending on the diameter of the lens in the optical adjustment component, the optical adjustment component may have a width which varies, ranging from 5 mm to 50 mm, such as from 6 mm to 45 mm, such as from 7 mm to 40 mm, such as from 8 mm to 35 mm, such as from 9 mm to 30 mm and including from 10 mm to 25 mm. For example, where the optical adjustment component is cylindrical, the diameter of the connector may be from 5 mm to 50 mm, such as from 6 mm to 45 mm, such as from 7 mm to 40 mm, such as from 8 mm to 35 mm, such as from 9 mm to 30 mm and including from 10 mm to 25 mm.

The aligners positioned at the distal end of the optical adjustment component are complimentary to the aligners of the connector such that coupling of the aligners and magnets of the optical adjustment component and the aligners and magnets of the connector is sufficient to position and maintain optical concentricity of the concentrator lens and the optical adjustment component lens. The optical adjustment component may include any number of aligners positioned at its distal end, so long as coupling of the aligners on the optical adjustment component to the aligners on the connector is sufficient to position and maintain optical concentricity of the concentrator lens and the optical adjustment component lens. For example, optical adjustment components of interest may include 2 or more aligners, such as 3 or more aligners, such as 4 or more aligners, such as 5 or more aligners, such as 7 or more aligners and including 10 or more aligners. Any suitable type of aligner may be employed, such as an alignment protrusion, an alignment rail, an alignment notch, an alignment groove, an alignment slot, an alignment hole or a combination thereof. For example, in some instances the optical adjustment component distal end includes one or more recesses, such as notches or holes. In other instances, the optical adjustment component distal end includes one or more protrusions. In certain instances, the optical adjustment component distal end includes one or more protrusions and one or more notches.

The shape of the aligner positioned at the distal end of the optical adjustment component may vary, where cross-sectional shapes of interest include, but are not limited to rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. In some embodiments, the aligners are recesses that are cylindrically shaped. In other embodiments, the aligners are recesses that are spherical. In yet other embodiments, the aligners are recesses that are polygonal-shaped. In still other embodiments, the aligners are notches that are polygonal-shaped, such as square or rectangular-shaped.

The width of each aligner may vary ranging from 1 mm to 25 mm, such as from 2 mm to 22 mm, such as from 3 mm to 20 mm, such as from 4 mm to 17 mm and including from 5 mm to 15 mm. The length of each aligner positioned at the distal end of the optical adjustment component ranges from 1 mm to 50 mm, such as from 2 mm to 45 mm, such as from 3 mm to 40 mm, such as from 4 m to 35 mm, such as from 5 mm to 30 mm and including from 10 mm to 20 mm. Where the aligner positioned at the distal end of the optical adjustment component is a recess, such as a notch, a slot, a groove or a hole, the depth of the aligner may also range from 1 mm to 50 mm, such as from 2 mm to 45 mm, such as from 3 mm to 40 mm, such as from 4 m to 35 mm, such as from 5 mm to 30 mm and including from 10 mm to 20 mm.

The aligners at the distal end of the optical adjustment component are positioned to couple with the aligners at the proximal end of the connector. In some embodiments, one or more aligners are positioned along the outer edge of the optical adjustment component distal end. In other embodiments, one or more aligners are positioned between the center and the outer edge of the optical adjustment component distal end, such as 1 mm or more from the outer edge of the optical adjustment component distal end, such as 2 mm or more, such as 3 mm or more, such as 4 mm or more and including 5 mm or more from the outer edge of the optical adjustment component distal end.

Where the optical adjustment component includes more than one aligner, the distance between each aligner may vary, such as being spaced apart by 2 mm or more, such as by 3 mm or more, such as by 5 mm or more, such as by 7 mm or more, such as by 10 mm or more and including by 25 mm or more. Where the optical adjustment component includes three or more aligners, the distance between each aligner may be the same or different or a combination thereof. In some embodiments, the distance between each aligner is different. In other embodiments, each aligner is spaced equidistant from each other. In certain embodiments, the optical adjustment component includes 3 aligners that are equidistantly spaced along the outer edge of the optical adjustment component distal end. For instance, the optical adjustment component may include 3 polygonal-shaped (e.g., square or rectangular) recesses (e.g., complimentary to 3-polygonal-shaped protrusions on the connector) which are spaced equidistantly from each other along the outer edge of the optical adjustment component distal end.

In some embodiments, the surfaces of the aligners at the distal end of the optical adjustment component are substantially flat to maximize contact with the surfaces of the aligners positioned on the proximal end of the connector. For example, as discussed above where the connector proximal end includes one or more protrusions, the outer walls (i.e., top and side surfaces) of the protrusions are substantially flat to maximize contact with the inner walls of recesses (e.g., bottom and side walls) in the optical adjustment component distal end. In these embodiments, the walls of the aligners at the distal end of the optical adjustment component exhibit little to no deviation along its surface, such as where crevices or protrusions along the aligner walls are 100 μm or less as measured from the wall surface, such as 50 μm or less, such as 25 μm or less, such as 15 μm or less, such as 10 μm or less, such as 5 μm or less, such as 2 μm or less, such as 1 μm or less, such as 0.5 μm or less, such as 0.1 μm or less, such as 0.05 μm or less, such as 0.01 μm or less, such as 0.005 μm or less and including by 0.001 μm or less as measured from the wall surface.

The distal end of the optical adjustment component also includes one or more magnets. Magnets of interest include, but are not limited to iron alloy materials having aluminum, nickel and colbalt (i.e., Alnico magnets), a ceramic or ferrite magnet, a rare-earth magnet such as samarium-cobalt magnets (e.g., $SmCo_5$), neodymium alloy (NdFeB) magnets (e.g., $Nd_2Fe_{14}B$) or a combination thereof. Depending on the size of the magnet, the magnet field produced by magnets of interest positioned at the optical adjustment component distal end range from 0.01 T to 10 T, or from 0.01 T to 5 T, or from 0.01 T to 2 T, or from 0.1 T to 2 T, or from 0.1 T to 1.5 T, including from 0.1 T to 1 T. The optical adjustment component may include any number of magnets, so long as coupling of the magnets on the optical adjustment component to the magnets on the connector is sufficient to maintain optical concentricity of the connector lens with the lens of the optical adjustment component. For example, the distal end of the optical adjustment component may include 2 or more magnets, such as 3 or more magnets, such as 4 or more magnets, such as 5 or more magnets, such as 7 or more magnets and including 10 or more magnets.

The shape of the magnets positioned at the distal end of the optical adjustment component may vary, where cross-sectional shapes of interest include, but are not limited to rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. In some embodiments, magnets of interest are cylindrically shaped. In other embodiments, the magnets are disk-shaped. In yet other embodiments, the magnets are square-shaped. In still other embodiments, the magnets are rectangular.

The width of each magnet may vary ranging from 1 mm to 25 mm, such as from 2 mm to 22 mm, such as from 3 mm to 20 mm, such as from 4 mm to 17 mm and including from 5 mm to 15 mm. The thickness of each magnet ranges from 0.01 mm to 10 mm, such as from 0.05 mm to 9 mm, such as from 0.1 mm to 8 mm, such as from 0.5 mm to 7 mm, such as from 1 mm to 6 mm and including from 2 mm to 5 mm. In some embodiments, magnets positioned at the distal end of the optical adjustment component are disk-shaped. In these embodiments, the disk-shaped magnets have a diameter ranging from 1 mm to 25 mm, such as from 2 mm to 22 mm, such as from 3 mm to 20 mm, such as from 4 mm to 17 mm and including from 5 mm to 15 mm and a thickness ranging from 0.01 mm to 10 mm, such as from 0.05 mm to 9 mm, such as from 0.1 mm to 8 mm, such as from 0.5 mm to 7 mm, such as from 1 mm to 6 mm and including from 2 mm to 5 mm.

The magnets may be positioned at any location on the distal end of the optical adjustment component. For example, in some embodiments one or more magnets are positioned adjacent to the aligner, such as 1 mm or more from the lens of the connector, such as 2 mm or more, such as 3 mm or more, such as 4 mm or more and including 5 mm or more from aligner. In other embodiments, one or more magnets are positioned along the outer edge of the optical adjustment component distal end. In still other embodiments, one or more magnets are positioned between the center and the outer edge of the optical adjustment component distal end, such as 1 mm or more from the outer edge of the optical adjustment component distal end, such as 2 mm or more, such as 3 mm or more, such as 4 mm or more and including 5 mm or more from the outer edge of the optical adjustment component distal end.

Where the distal end of the optical adjustment component includes more than one magnet, the distance between each magnet may vary, such as where the magnets are spaced apart by 2 mm or more, such as by 3 mm or more, such as by 5 mm or more, such as by 7 mm or more, such as by 10 mm or more and including by 25 mm or more. Where three or more magnets are positioned on the optical adjustment component distal end, the distances between each magnet may be the same or different or a combination thereof. In some embodiments, the distance between each magnet is different. In other embodiments, the magnets are spaced equidistant from each other. In certain embodiments, the optical adjustment component includes 3 magnets that are equidistantly spaced along the outer edge of the optical adjustment component distal end. For instance, the optical adjustment component may include 3 disk-shaped magnets which are spaced equidistantly from each other along the outer edge of the optical adjustment component distal end.

The top surface of magnets positioned at the optical adjustment component distal end contacts the top surface of magnets positioned at the proximal end of the connector. In some embodiments, the top surface of the magnets is substantially flat to maximize contact between the magnets of the connector and the magnets of the optical adjustment component. In these embodiments, the top surface of the magnets exhibits little to no deviation along its surface, such as where crevices or protrusions along the magnet top surface deviate from by 100 µm or less as measured from the top surface, such as 50 µm or less, such as 25 µm or less, such as 15 µm or less, such as 10 µm or less, such as 5 µm or less, such 2 µm or less, such as 1 µm or less, such as 0.5 µm or less, such as 0.1 µm or less, such as 0.05 µm or less, such as 0.01 µm or less, such as 0.005 µm or less and including by 0.001 µm or less as measured from top surface.

Figure 3:
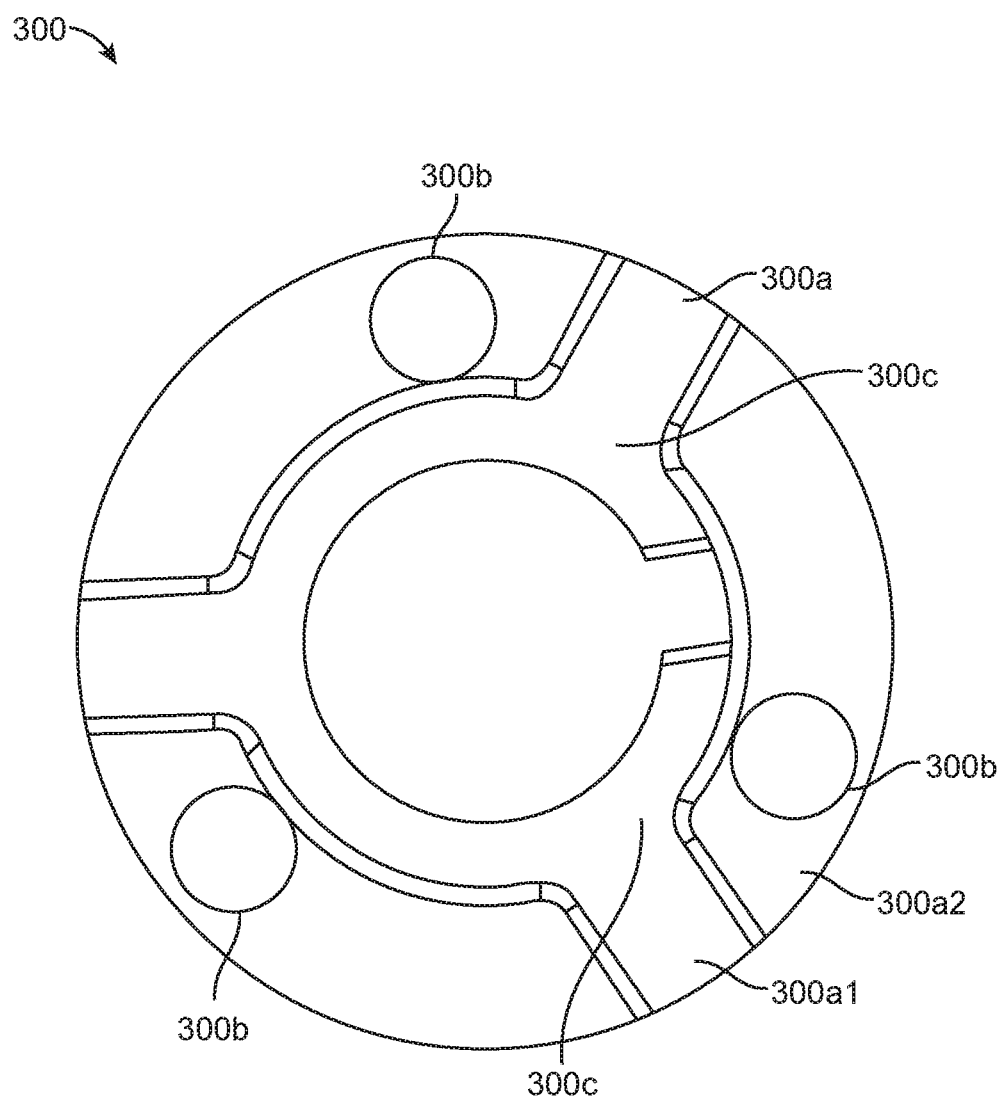
FIG. 3 depicts a top-view of the distal end of an optical adjustment component according to certain embodiments.

FIG. 3 depicts a top-view of the distal end of an optical adjustment component according to certain embodiments. Optical adjustment component 300 includes three aligners 300a and three magnets 300b. Aligners 300a are polygonal shaped notches in the optical adjustment component distal end and are positioned along the outer edge at equal distances from each other. Each alignment notch 300a includes a bottom surface 300a1 and side walls 300a2 which contact the side surfaces of the protrusions at the proximal end of the connector (as described above). FIG. 3 also shows surface 300c at the distal end of the optical adjustment component which contacts a surface at the proximal end of the connector when the aligners and magnets of the connector and the aligners and magnets of the optical adjustment component are coupled together.

As summarized above, the optical adjustment component includes one or more lenses that are optically concentric with the lens on the connector when the aligners and magnets on the connector are coupled to the aligners and magnets on the optical adjustment component. In embodiments, the optical adjustment component lens may be a collimating lens, a focusing lens, a magnifying lens, a de-magnifying lens, or some other lens. In some embodiments, the optical adjustment component includes a focusing lens. In other embodiments, the optical adjustment component includes one or more collimating lenses. For example, the optical adjustment component in certain instances includes a single collimating lens. In other instances, the optical adjustment component includes two collimating lenses.

Depending on the size of the optical adjustment component, the width of the lens may vary, ranging from 5 mm to 50 mm, such as from 6 mm to 45 mm, such as from 7 mm to 40 mm, such as from 8 mm to 35 mm, such as from 9 mm to 30 mm and including from 10 mm to 25 mm. The numerical aperture of the subject lenses may also vary, ranging from 0.01 to 2.0, such as from 0.05 to 1.9, such as from 0.1 to 1.8, such as from 0.2 to 1.7, such as from 0.3 to 1.6, and including a numerical aperture ranging from 0.5 to 1.5. Likewise, the focal length of the objective lens varies, ranging from 0.1 mm to 20 mm, such as from 0.5 mm to 19 mm, such as from 1 mm to 18 mm and including from 2 mm to 15 mm.

In certain embodiments, the optical adjustment component includes one or more additional light adjusting devices. By "light adjusting" is meant that the light passing through the optical adjustment component is changed as desired before being conveyed beyond the proximal end of the optical adjustment component (e.g., to a detector for measurement, as described below). For example light adjusting devices of interest may increase or decrease the dimensions of the propagated beam of light, change the direction of light propagation or change the wavelengths of the light.

Light adjusting devices may be any convenient structure which provides the desired change in the propagated light and may include, but are not limited to, additional lenses, mirrors, filters, pinholes, slits, gratings, light refractors, filters and any combinations thereof. The optical adjustment component may include one or more additional light adjusting devices as needed, such as two or more, such as three or more, such as four or more and including five or more additional light adjusting devices.

In some embodiments, the light adjusting devices are not physically in contact with the optical adjustment component. The light adjusting device may be positioned from the proximal end of the optical adjustment component a distance that is 0.05 mm or more, 0.1 mm or more, such as 0.2 mm or more, such as 0.5 mm or more, such as 1 mm or more, such as 5 mm or more, such as 10 mm or more, such as 25 mm or more, such as 50 mm or more, including 100 mm or more. In other embodiments, the optical adjustment component is physically coupled to the optical adjustment component, such as with an adhesive. In some instances, the light adjusting device is releasably attached to the optical adjustment component. In these embodiments, the one or more light adjusting devices are freely detached and re-attached to the optical adjustment component. Where the light adjusting device is configured to be releasably attached to an optical adjustment component, the optical adjustment component may include one or more fasteners for attaching the light adjusting device to the optical adjustment component. Suitable fasteners may include, but are not limited to, hook and loop fasteners, latches, notches, grooves, pins, tethers, hinges, Velcro, non-permanent adhesives or a combination thereof.

In certain embodiments, the light adjusting device is a wavelength separator. The term "wavelength separator" is used herein in its conventional sense to refer to a device that separates polychromatic light into its component wavelengths. Wavelength separation, according to certain embodiments, may include selectively passing or blocking specific wavelengths or wavelength ranges of the polychromatic light. Wavelength separation devices of interest include but are not limited to, colored glass, bandpass filters, interference filters, dichroic mirrors, diffraction gratings, monochromators and combinations thereof, among other wavelength separating devices. In certain instances, the light adjusting device includes one or more bandpass filters having minimum bandwidths ranging from 2 nm to 100 nm, such as from 3 nm to 95 nm, such as from 5 nm to 95 nm, such as from 10 nm to 90 nm, such as from 12 nm to 85 nm, such as from 15 nm to 80 nm and including bandpass filters having minimum bandwidths ranging from 20 nm to 50 nm.

As discussed above, the subject optically aligned light collection systems are configured to maintain optical alignment of the two or more releasably attachable components (i.e., connector and optical adjustment component). In embodiments, the subject optically aligned light collection systems are configured to maintain optical alignment, as desired, such as until one or more components are deliberately and physically detached from the other component. For example, the subject optically aligned light collection systems are configured to maintain optical alignment of the two components for a duration of 1 hour or longer, such as 4 hours or longer, such as 6 hours or longer, such as 12 hours or longer, such as 18 hours or longer, such as 24 hours or longer, such as 3 days or longer, such as 7 days or longer, such as 2 weeks or longer and including for 1 month or longer.

Systems for Measuring Light Emitted by a Sample

Aspects of the present disclosure also include systems for measuring light from a sample (e.g., in the flow stream in a flow cytometer). In certain embodiments, systems include a light source, a detector and one or more of the subject optically aligned light collection systems for collecting light emitted by the sample, as described above. For example, systems of interest may include a light source, a detector and an optically aligned light collection system (as described above) that includes: a flow cell nozzle having a nozzle chamber having a proximal end and distal end, one or more aligners, one or more magnets and a lens positioned at the proximal end of the nozzle chamber and a nozzle orifice positioned at the distal end of the nozzle chamber and an optical adjustment component coupled to the flow cell nozzle through the aligners and magnets. In some embodiments, the system is a flow cytometer. In some instances, the proximal end of the optical adjustment component is non-releasably integrated into the flow cytometer. In certain embodiments, the flow cell nozzle (as described above) is configured to propagate light emitted by a sample in the flow stream upstream through the nozzle orifice by total internal reflectance.

Systems of interest for measuring light from a sample include a light source. In embodiments, the light source may be any suitable broadband or narrow band source of light. Depending on the components in the sample (e.g., cells, beads, non-cellular particles, etc.), the light source may be configured to emit wavelengths of light that vary, ranging from 200 nm to 1500 nm, such as from 250 nm to 1250 nm, such as from 300 nm to 1000 nm, such as from 350 nm to 900 nm and including from 400 nm to 800 nm. For example, the light source may include a broadband light source emitting light having wavelengths from 200 nm to 900 nm. In other instances, the light source includes a narrow band light source emitting a wavelength ranging from 200 nm to 900 nm. For example, the light source may be a narrow band LED (1 nm-25 nm) emitting light having a wavelength ranging between 200 nm to 900 nm. In some embodiments, the light source is a laser, such as continuous wave laser. For example, the laser may be a helium-neon (HeNe) laser. In certain embodiments, the light source is a laser in a flow cytometer.

In other embodiments, the light source is a non-laser light source, such as a lamp, including but not limited to a halogen lamp, deuterium arc lamp, xenon arc lamp, a light-emitting diode, such as a broadband LED with continuous spectrum, superluminescent emitting diode, semiconductor light emitting diode, wide spectrum LED white light source, an multi-LED integrated. In some instances the non-laser light source is a stabilized fiber-coupled broadband light source, white light source, among other light sources or any combination thereof.

The light source may be positioned any suitable distance from the sample (e.g., the flow stream in a flow cytometer), such as at a distance of 0.001 mm or more from the flow stream, such as 0.005 mm or more, such as 0.01 mm or more, such as 0.05 mm or more, such as 0.1 mm or more, such as 0.5 mm or more, such as 1 mm or more, such as 5 mm or more, such as 10 mm or more, such as 25 mm or more and including at a distance of 100 mm or. In addition, the light source irradiate the sample at any suitable angle (e.g., relative the vertical axis of the flow stream), such as at an angle ranging from 10° to 90°, such as from 15° to 85°, such as from 20° to 80°, such as from 25° to 75° and including from 30° to 60°, for example at a 90° angle.

The light source may be configured to irradiate the sample continuously or in discrete intervals. In some instances, systems include a light source that is configured to irradiate the sample continuously, such as with a continuous wave laser that continuously irradiates the flow stream at the interrogation point in a flow cytometer. In other instances, systems of interest include a light source that is configured to irradiate the sample at discrete intervals, such as every 0.001 milliseconds, every 0.01 milliseconds, every 0.1 milliseconds, every 1 millisecond, every 10 milliseconds, every 100 milliseconds and including every 1000 milliseconds, or some other interval. Where the light source is configured to irradiate the sample at discrete intervals, systems may include one or more additional components to provide for intermittent irradiation of the sample with the light source. For example, the subject systems in these embodiments may include one or more laser beam choppers, manually or computer controlled beam stops for blocking and exposing the sample to the light source.

In some embodiments, light emitted by the sample is collected and propagated through the optically aligned flow cell nozzle and optical adjustment component (as described above) and onto a detector. Detectors of interest may include, but are not limited to optical sensors or photodetectors, such as active-pixel sensors (APSs), avalanche photodiode, image sensors, charge-coupled devices (CODs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, the collected light is measured with a charge-coupled device (CCD), semiconductor charge-coupled devices (CCD), active pixel sensors (APS), complementary metal-oxide semiconductor (CMOS) image sensors or N-type metal-oxide semiconductor (NMOS) image sensors. In some embodiments, the imaging sensor is a CCD camera. For example, the camera may be an electron multiplying CCD (EMCCD) camera or an intensified CCD (ICCD) camera. In other embodiments, the imaging sensor is a CMOS-type camera. Where the collected light is measured with a CCD, the active detecting surface area of the CCD may vary, such as from 0.01 $cm^2$ to 10 $cm^2$, such as from 0.05 $cm^2$ to 9 $cm^2$, such as from, such as from 0.1 $cm^2$ to 8 $cm^2$, such as from 0.5 $cm^2$ to 7 $cm^2$ and including from 1 $cm^2$ to 5 $cm^2$. The number of photodetectors in the subject systems may vary, as desired. For example, the subject systems may include one photodetector or more, such as two photodetectors or more, such as three photodetectors or more, such as four photodetectors or more, such as five photodetectors or more and including ten photodetectors or more. In certain embodiments, systems include one photodetector. In other embodiments, systems include two photodetectors.

Where the subject systems include more than one photodetector, each photodetector may be the same, or the collection of two or more photodetectors may be a combination of different photodetectors. For example, where the subject systems include two photodetectors, in some embodiments the first photodetector is a CCD-type device and the second photodetector (or imaging sensor) is a CMOS-type device. In other embodiments, both the first and second photodetectors are CCD-type devices. In yet other embodiments, both the first and second photodetectors are CMOS-type devices. In still other embodiments, the first photodetector is a CCD-type device and the second photodetector is a photomultiplier tube. In still other embodiments, the first photodetector is a CMOS-type device and the second photodetector is a photomultiplier tube. In yet other embodiments, both the first and second photodetectors are photomultiplier tubes.

In embodiments of the present disclosure, detectors of interest are configured to measure collected light at one or more wavelengths, such as at 2 or more wavelengths, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring light emitted by a sample in the flow stream at 400 or more different wavelengths.

In some embodiments, detectors of interest are configured to measure collected light over a range of wavelengths (e.g., 200 nm-1000 nm). In certain embodiments, detectors of interest are configured to collect spectra of light over a range of wavelengths. For example, systems may include one or more detectors configured to collect spectra of light over one or more of the wavelength ranges of 200 nm-1000 nm. In yet other embodiments, detectors of interest are configured to measure light emitted by a sample in the flow stream at one or more specific wavelengths. For example, systems may include one or more detectors configured to measure light at one or more of 450 nm, 518 nm, 519 nm, 561 nm, 578 nm, 605 nm, 607 nm, 625 nm, 650 nm, 660 nm, 667 nm, 670 nm, 668 nm, 695 nm, 710 nm, 723 nm, 780 nm, 785 nm, 647 nm, 617 nm and any combinations thereof. In certain embodiments, one or more detectors may be configured to be paired with specific fluorophores, such as those used with the sample in a fluorescence assay.

In embodiments, the detector is configured to measure light continuously or in discrete intervals. In some instances, detectors of interest are configured to take measurements of the collected light continuously. In other instances, detectors of interest are configured to take measurements in discrete intervals, such as measuring light every 0.001 millisecond, every 0.01 millisecond, every 0.1 millisecond, every 1 millisecond, every 10 milliseconds, every 100 milliseconds and including every 1000 milliseconds, or some other interval.

In certain embodiments, the subject systems are flow cytometric systems employing the above described optically aligned light collection system (e.g., flow cell nozzle optically aligned to an optical adjustment component) for detecting light emitted by a sample in a flow stream by total internal reflectance. Suitable flow cytometry systems and methods for analyzing samples include, but are not limited to those described in Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); *Practical Flow Cytometry*, 3rd ed., Wiley-Liss (1995); Virgo, et al. (2012) *Ann Clin Biochem*. January; 49(pt 1):17-28; Linden, et. al., *Semin Throm Hemost*. 2004 October; 30(5):502-11; Alison, et al. *J Pathol*, 2010 December; 222(4):335-344; and Herbig, et al. (2007) *Crit Rev Ther Drug Carrier Syst*. 24(3): 203-255; the disclosures of which are incorporated herein by reference. In certain instances, flow cytometry systems of interest include BD Biosciences FACSCanto™ flow cytometer, BD Biosciences FACSVantage™, BD Biosciences FACSort™, BD Biosciences FACSCount™, BD Biosciences FACScan™, and BD Biosciences FACSCalibur™ systems, a BD Biosciences Influx™ cell sorter, BD Biosciences Jazz™ cell sorter and BD Biosciences Aria™ cell sorter or the like.

In certain embodiments, the subject systems are flow cytometer systems which incorporate one or more components of the flow cytometers described in U.S. Pat. Nos. 3,960,449; 4,347,935; 4,667,830; 4,704,891; 4,770,992; 5,030,002; 5,040,890; 5,047,321; 5,245,318; 5,317,162; 5,464,581; 5,483,469; 5,602,039; 5,620,842; 5,627,040; 5,643,796; 5,700,692; 6,372,506; 6,809,804; 6,813,017; 6,821,740; 7,129,505; 7,201,875; 7,544,326; 8,140,300; 8,233,146; 8,753,573; 8,975,595; 9,092,034; 9,095,494 and 9,097,640; the disclosures of which are herein incorporated by reference.

In certain embodiments, flow cytometers of interest are configured to include a flow cell nozzle which is configured to propagate light emitted by a sample in a flow stream upstream through the nozzle orifice by total internal reflectance. The term "propagate" is used herein in its conventional sense to refer to the travel of light through the fluid medium of the flow stream where the path of propagated light is a function of the refraction, reflection, diffraction and interference by the fluid medium. In these embodiments, the flow cytometer includes a flow cell nozzle that propagates and collects light in a direction which is opposite to the direction of fluid flow by the flow stream. In other words, where the flow stream has fluidic flow along the positive Y direction along the Y axis in an X-Y plane, light signals from light propagated upstream by total internal reflectance traverses in the negative Y direction. The phrase "total internal reflectance" is used herein in its conventional sense to refer to the propagation of electromagnetic waves within the boundaries of a fluid medium (e.g., flow stream) such that when a propagating wave strikes the medium boundary at an angle larger than the critical angle with respect to the normal to the surface, the electromagnetic wave is internally reflected.

Flow cell nozzles according to these embodiments includes a nozzle chamber having a proximal end where light propagated upstream is collected and a distal end having a nozzle orifice in fluid communication with the flow stream. In some instances, the flow cell nozzle includes a proximal cylindrical portion defining a longitudinal axis and a distal frustoconical portion which terminates in a flat surface having the nozzle orifice that is transverse to the longitudinal axis. The angle of the frustoconical walls of the flow nozzle relative to the longitudinal axis of the flow stream may vary, in certain embodiments, ranging from 120° to 160°. In certain embodiments, the walls of the nozzle chamber are reflective. The proximal end of the flow cell nozzle in flow cytometers of interest may include a sample injection port to provide sample (e.g., a biological sample) to the flow cell and a sheath fluid injection port which provides sheath fluid to the flow cell nozzle.

In some instances, the flow cell nozzle includes one or more optical adjustment components. By "optical adjustment" is meant that emitted light propagated upstream from the flow stream through the nozzle orifice is changed as desired before being conveyed to a detector (as discussed in greater detail below) for measurement. For example, the optical adjustment may be to increase the dimensions of the collected beam of light, to focus the collected beam of light onto the surface of a detector or to collimate the beam of light. In some instances, optical adjustment is a magnification protocol so as to increase the beam spot produced by the light beam propagated through the nozzle orifice by total internal reflectance within the flow stream. In other instances, optical adjustment is a focusing protocol to reduce the dimensions of the beam spot.

In some embodiments, flow cell nozzles and flow cytometer systems of interest that are configured to propagate light emitted by a sample upstream through the flow stream by total internal reflectance include those described in U.S. patent application Ser. No. 14/260,177 filed on Apr. 23, 2014, the disclosure of which is herein incorporated by reference.

In some embodiments, the subject systems include flow cytometer systems that also employ the imaging sensors and optics subsystems described herein to assess alignment of the light source with the flow stream. The phrase "assessing alignment" is used herein in its conventional sense to refer to determining the relative position of irradiation on the flow stream by the light source. In some embodiments, assessing alignment of the light source with the flow stream includes determining the position of irradiation by the light source along the horizontal axis of the flow stream. As discussed above, systems of interest may include one or more light sources (e.g., laser, such as a diode laser) and one or more position sensing detectors (e.g., quadrant photodiode or wedge detector) Systems of interest according to these embodiments may also include in the memory operably coupled to the processor, instructions to calculate a differential signal amplitude between a first light signal and a second light signal to assess alignment of a light source (e.g., laser) with a flow stream. In embodiments, the processor is configured to execute instructions from memory for assessing alignment of the light source with the flow stream and in some instances, adjust the position of the light source to match a position which produces the maximal differential signal amplitude between the first light signal and the second light signal from the irradiated flow stream. The memory operably coupled to processors described herein may include a plurality of instructions for detecting first and second light signals at different times along a vertical axis of the irradiated flow stream, calculating a differential signal amplitude between the first signal and second signal and assessing alignment of the light source with the flow stream based on the calculated differential signal amplitude between the first light signal and second light signal.

In some instances, the processor memory described herein further includes algorithm for determining a maximal differential signal amplitude to assess alignment of the flow stream with the light source. For example, the processor memory may include algorithm for determining the position of irradiation by the light source on the flow stream that produces the maximal differential signal amplitude between the first light signal and the second lights signal. In this example, systems of interest may use one or more image capturing sensors described herein for mapping the spatial position of the irradiation on the flow stream in an X-Y plane. In some instances, the subject systems are configured to adjust the position of the light source in response to the assessed alignment between the light source and the flow stream. The subject systems may also be configured to automatically align the light source with flow stream.

In some embodiments, systems of interest that are configured to assess the alignment of a light source with the flow stream include those described in U.S. Provisional Patent Application No. 62/091,421 filed on Dec. 12, 2014, the disclosure of which is herein incorporated by reference. In some embodiments, the flow cytometers are flow cytometers that include one or more components from the cytometers described in: U.S. application Ser. No. 14/260,177 published as US2014/0320861 and U.S. Provisional Application Ser. No. 62/091,421; the disclosures of which are herein incorporated by reference.

Methods for Measuring Light Emitted by a Sample

Aspects of the disclosure also include methods for measuring light emitted from a sample (e.g., in the flow stream in a flow cytometer). In certain embodiments, methods include measuring light emitted by a sample in a flow stream which is propagated upstream through the flow cell nozzle orifice by total internal reflectance by the fluid medium of the flow stream. In some embodiments, the sample is a biological sample. The term "biological sample" is used in its conventional sense to refer to a whole organism, plant, fungi or a subset of animal tissues, cells or component parts which may in certain instances be found in blood, mucus, lymphatic fluid, synovial fluid, cerebrospinal fluid, saliva, bronchoalveolar lavage, amniotic fluid, amniotic cord blood, urine, vaginal fluid and semen. As such, a "biological sample" refers to both the native organism or a subset of its tissues as well as to a homogenate, lysate or extract prepared from the organism or a subset of its tissues, including but not limited to, for example, plasma, serum, spinal fluid, lymph fluid, sections of the skin, respiratory, gastrointestinal, cardiovascular, and genitourinary tracts, tears, saliva, milk, blood cells, tumors, organs. Biological samples may be any type of organismic tissue, including both healthy and diseased tissue (e.g., cancerous, malignant, necrotic, etc.). In certain embodiments, the biological sample is a liquid sample, such as blood or derivative thereof, e.g., plasma, tears, urine, semen, etc., where in some instances the sample is a blood sample, including whole blood, such as blood obtained from venipuncture or fingerstick (where the blood may or may not be combined with any reagents prior to assay, such as preservatives, anticoagulants, etc.).

In certain embodiments the source of the sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. The methods may be applied to samples obtained from human subjects of both genders and at any stage of development (i.e., neonates, infant, juvenile, adolescent, adult), where in certain embodiments the human subject is a juvenile, adolescent or adult. While the present invention may be applied to samples from a human subject, it is to be understood that the methods may also be carried-out on samples from other animal subjects (that is, in "non-human subjects") such as, but not limited to, birds, mice, rats, dogs, cats, livestock and horses.

In practicing methods according to certain embodiments, a sample (e.g., in a flow stream of a flow cytometer) is irradiated with light from a light source. In some embodiments, the light source is a broadband light source, emitting light having a broad range of wavelengths, such as for example, spanning 50 nm or more, such as 100 nm or more, such as 150 nm or more, such as 200 nm or more, such as 250 nm or more, such as 300 nm or more, such as 350 nm or more, such as 400 nm or more and including spanning 500 nm or more. For example, one suitable broadband light source emits light having wavelengths from 200 nm to 1500 nm. Another example of a suitable broadband light source includes a light source that emits light having wavelengths from 400 nm to 1000 nm. Where methods include irradiating with a broadband light source, broadband light source protocols of interest may include, but are not limited to, a halogen lamp, deuterium arc lamp, xenon arc lamp, stabilized fiber-coupled broadband light source, a broadband LED with continuous spectrum, superluminescent emitting diode, semiconductor light emitting diode, wide spectrum LED white light source, an multi-LED integrated white light source, among other broadband light sources or any combination thereof.

In other embodiments, methods includes irradiating with a narrow band light source emitting a particular wavelength or a narrow range of wavelengths, such as for example with a light source which emits light in a narrow range of wavelengths like a range of 50 nm or less, such as 40 nm or less, such as 30 nm or less, such as 25 nm or less, such as 20 nm or less, such as 15 nm or less, such as 10 nm or less, such as 5 nm or less, such as 2 nm or less and including light sources which emit a specific wavelength of light (i.e., monochromatic light). Where methods include irradiating with a narrow band light source, narrow band light source protocols of interest may include, but are not limited to, a narrow wavelength LED, laser diode or a broadband light source coupled to one or more optical bandpass filters, diffraction gratings, monochromators or any combination thereof.

In certain embodiments, methods include irradiating the sample with one or more lasers. As discussed above, the type and number of lasers will vary depending on the sample as well as desired light collected and may be a gas laser, such as a helium-neon laser, argon laser, krypton laser, xenon laser, nitrogen laser, $CO_2$ laser, CO laser, argon-fluorine (ArF) excimer laser, krypton-fluorine (KrF) excimer laser, xenon chlorine (XeCl) excimer laser or xenon-fluorine (XeF) excimer laser or a combination thereof. In others instances, the methods include irradiating the flow stream with a dye laser, such as a stilbene, coumarin or rhodamine laser. In yet other instances, methods include irradiating the flow stream with a metal-vapor laser, such as a helium-cadmium (HeCd) laser, helium-mercury (HeHg) laser, helium-selenium (HeSe) laser, helium-silver (HeAg) laser, strontium laser, neon-copper (NeCu) laser, copper laser or gold laser and combinations thereof. In still other instances, methods include irradiating the flow stream with a solid-state laser, such as a ruby laser, an Nd:YAG laser, NdCrYAG laser, Er:YAG laser, Nd:YLF laser, Nd:YVO$_4$ laser, Nd:YCa$_4$O(BO$_3$)$_3$ laser, Nd:YCOB laser, titanium sapphire laser, thulim YAG laser, ytterbium YAG laser, ytterbium$_2$O$_3$ laser or cerium doped lasers and combinations thereof.

The sample may be irradiated with one or more of the above mentioned light sources, such as two or more light sources, such as three or more light sources, such as four or more light sources, such as five or more light sources and including ten or more light sources. The light source may include any combination of types of light sources. For example, in some embodiments, the methods include irradiating the sample in the flow stream with an array of lasers, such as an array having one or more gas lasers, one or more dye lasers and one or more solid-state lasers.

The sample may be irradiated with wavelengths ranging from 200 nm to 1500 nm, such as from 250 nm to 1250 nm, such as from 300 nm to 1000 nm, such as from 350 nm to 900 nm and including from 400 nm to 800 nm. For example, where the light source is a broadband light source, the sample may be irradiated with wavelengths from 200 nm to 900 nm. In other instances, where the light source includes a plurality of narrow band light sources, the sample may be irradiated with specific wavelengths in the range from 200 nm to 900 nm. For example, the light source may be plurality of narrow band LEDs (1 nm-25 nm) each independently emitting light having a range of wavelengths between 200 nm to 900 nm. In other embodiments, the narrow band light source includes one or more lasers (such as a laser array) and the sample is irradiated with specific wavelengths ranging from 200 nm to 700 nm, such as with a laser array having gas lasers, excimer lasers, dye lasers, metal vapor lasers and solid-state laser as described above.

Where more than one light source is employed, the sample may be irradiated with the light sources simultaneously or sequentially, or a combination thereof. For example, the sample may be simultaneously irradiated with both light sources. In other embodiments, the flow stream is sequentially irradiated with both light sources. Where two light sources irradiate sequentially, the time each light source irradiates the sample may independently be 0.001 microseconds or more, such as 0.01 microseconds or more, such as 0.1 microseconds or more, such as 1 microsecond or more, such as 5 microseconds or more, such as 10 microseconds or more, such as 30 microseconds or more and including 60 microseconds or more. For example, methods may include irradiating the sample with the light source (e.g. laser) for a duration which ranges from 0.001 microseconds to 100 microseconds, such as from 0.01 microseconds to 75 microseconds, such as from 0.1 microseconds to 50 microseconds, such as from 1 microsecond to 25 microseconds and including from 5 microseconds to 10 microseconds. In embodiments where sample is sequentially irradiated with two or more light sources, the duration sample is irradiated by each light source may be the same or different.

The time period between irradiation by each light source may also vary, as desired, being separated independently by a delay of 0.001 microseconds or more, such as 0.01 microseconds or more, such as 0.1 microseconds or more, such as 1 microsecond or more, such as 5 microseconds or more, such as by 10 microseconds or more, such as by 15 microseconds or more, such as by 30 microseconds or more and including by 60 microseconds or more. For example, the time period between irradiation by each light source may range from 0.001 microseconds to 60 microseconds, such as from 0.01 microseconds to 50 microseconds, such as from 0.1 microseconds to 35 microseconds, such as from 1 microsecond to 25 microseconds and including from 5 microseconds to 10 microseconds. In certain embodiments, the time period between irradiation by each light source is 10 microseconds. In embodiments where sample is sequentially irradiated by more than two (i.e., three or more) light sources, the delay between irradiation by each light source may be the same or different.

The sample may be irradiated continuously or in discrete intervals. In some instances, methods include irradiating the sample in the sample with the light source continuously. In other instances, the sample in is irradiated with the light source in discrete intervals, such as irradiating every 0.001 millisecond, every 0.01 millisecond, every 0.1 millisecond, every 1 millisecond, every 10 milliseconds, every 100 milliseconds and including every 1000 milliseconds, or some other interval.

Depending on the light source, the sample may be irradiated from a distance which varies such as 0.01 mm or more, such as 0.05 mm or more, such as 0.1 mm or more, such as 0.5 mm or more, such as 1 mm or more, such as 2.5 mm or more, such as 5 mm or more, such as 10 mm or more, such as 15 mm or more, such as 25 mm or more and including 50 mm or more. Also, the angle or irradiation may also vary, ranging from 10° to 90°, such as from 15° to 85°, such as from 20° to 80°, such as from 25° to 75° and including from 30° to 60°, for example at a 90° angle.

As discussed above, in embodiments light emitted by the sample is passed through an optically aligned light collection system as described herein and measured by one or more detectors. In practicing the subject methods, the light propagated through the optically aligned light collection system (e.g., a flow cell nozzle configured to propagate light upstream by total internal reflectance coupled to an optical adjustment component) is measured at one or more wavelengths, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring the collected light at 400 or more different wavelengths.

In some embodiments, methods include measuring the collected light over a range of wavelengths (e.g., 200 nm-1000 nm). For example, methods may include collecting spectra of light over one or more of the wavelength ranges of 200 nm-1000 nm. In yet other embodiments, methods include measuring collected light at one or more specific wavelengths. For example, the collected light may be measured at one or more of 450 nm, 518 nm, 519 nm, 561 nm, 578 nm, 605 nm, 607 nm, 625 nm, 650 nm, 660 nm, 667 nm, 670 nm, 668 nm, 695 nm, 710 nm, 723 nm, 780 nm, 785 nm, 647 nm, 617 nm and any combinations thereof. In certain embodiments, methods including measuring wavelengths of light which correspond to the fluorescence peak wavelength of certain fluorophores.

The collected light may be measured continuously or in discrete intervals. In some instances, methods include taking measurements of the light continuously. In other instances, the light is measured in discrete intervals, such as measuring light every 0.001 millisecond, every 0.01 millisecond, every 0.1 millisecond, every 1 millisecond, every 10 milliseconds, every 100 milliseconds and including every 1000 milliseconds, or some other interval.

Measurements of the collected light may be taken one or more times during the subject methods, such 2 or more times, such as 3 or more times, such as 5 or more times and including 10 or more times. In certain embodiments, the light propa is measured two or more times, with the data in certain instances being averaged.

Light measurements may be taken with any convenient protocol, including but not limited to optical sensors or photodetectors, such as active-pixel sensors (APSs), avalanche photodiode, image sensors, charge-coupled devices (CODs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, the transmitted light is measured with a charge-coupled device (CCD), semiconductor charge-coupled devices (CCD), active pixel sensors (APS), complementary metal-oxide semiconductor (CMOS) image sensors or N-type metal-oxide semiconductor (NMOS) image sensors. In certain embodiments, light is measured with a charge-coupled device (CCD). Where the transmitted light is measured with a CCD, the active detecting surface area of the CCD may vary, such as from 0.01 $cm^2$ to 10 $cm^2$, such as from 0.05 $cm^2$ to 9 $cm^2$, such as from, such as from 0.1 $cm^2$ to 8 $cm^2$, such as from 0.5 $cm^2$ to 7 $cm^2$ and including from 1 $cm^2$ to 5 $cm^2$.

In some embodiments, methods include adjusting the light before measurement with the detector. For example, the collected light may be passed through one or more additional lenses, mirrors, pinholes, slits, gratings, light refractors, and any combinations thereof. In some instances, the collected light is passed through one or more focusing lenses, such as to reduce the profile of the light directed onto the active surface of the detector. In other instances, the emitted light from the sample is passed through one or more de-magnifying lenses, such as to increase the profile of the light directed onto the active surface of the detector.

In yet other instances, methods include further collimating the light. For example, light propagated through the subject optically aligned light collection systems may be further collimated by passing the light through one or more collimating lenses or with collimating mirrors or a combination thereof. In still other instances, methods further include passing light propagated through the subject optically aligned light collection systems through one or more wavelength separators. Wavelength separation, according to certain embodiments, may include selectively passing or blocking specific wavelengths or wavelength ranges of the polychromatic light. To separate wavelengths of light, the light may be passed through any convenient wavelength separating protocol, including but not limited to colored glass, bandpass filters, interference filters, dichroic mirrors, diffraction gratings, monochromators and combinations thereof, among other wavelength separating protocols.

In certain embodiments, light propagated through the subject optically aligned light collection systems may be further passed through fiber optics. As discussed above, suitable fiber optics protocols propagating light to the active surface of the detector include, but is not limited to, flow cytometer fiber optics protocols such as those described in U.S. Pat. No. 6,809,804, the disclosure of which is herein incorporated by reference.

Kits

Aspects of the invention further include kits, where kits include one or more connectors, optical adjustment components and flow cell nozzles as described herein. In some instances, the kits can include one or more assay components (e.g., labeled reagents, buffers, etc., such as described above). In some instances, the kits may further include a sample collection device, e.g., a lance or needle configured to prick skin to obtain a whole blood sample, a pipette, etc., as desired.

The various assay components of the kits may be present in separate containers, or some or all of them may be pre-combined. For example, in some instances, one or more components of the kit, e.g., the flow cell nozzles, are present in a sealed pouch, e.g., a sterile foil pouch or envelope.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), portable flash drive, and the like, on which the information has been recorded. Yet another form of these instructions that may be present is a website address which may be used via the internet to access the information at a removed site.

Utility

The subject methods for aligning components of a light collection system and optically aligned light collection systems thereof find use in a variety of application where it is desirable to increase the amount of emitted light measured by a sample in a fluid medium. In certain embodiments, the present disclosure finds use in enhancing measurements of light emitted by a sample in flow stream of a flow cytometer. Embodiments of the present disclosure find use where enhancing the effectiveness of emission measurements in flow cytometry are desired, such as in research and high throughput laboratory testing. The present disclosure also finds use where it is desirable to provide a flow cytometer with improved cell sorting accuracy, enhanced particle collection, reduced energy consumption, particle charging efficiency, more accurate particle charging and enhanced particle deflection during cell sorting.

The present disclosure also finds use in applications where cells prepared from a biological sample may be desired for research, laboratory testing or for use in therapy. In some embodiments, the subject methods and devices may facilitate the obtaining individual cells prepared from a target fluidic or tissue biological sample. For example, the subject methods and systems facilitate obtaining cells from fluidic or tissue samples to be used as a research or diagnostic specimen for diseases such as cancer. Likewise, the subject methods and systems facilitate obtaining cells from fluidic or tissue samples to be used in therapy. Methods and devices of the present disclosure allow for separating and collecting cells from a biological sample (e.g., organ, tissue, tissue fragment, fluid) with enhanced efficiency and low cost as compared to traditional flow cytometry systems.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of optically aligning a light collection system, comprising:
   coupling a flow cell nozzle to an optical adjustment component by connecting a first magnet and first aligner positioned on a proximal end of the flow cell nozzle to a second magnet and second aligner positioned on the optical adjustment component,
   wherein the flow cell nozzle comprises:
      a nozzle chamber having a proximal end and a distal end;
      a nozzle orifice positioned at the distal end of the nozzle chamber; and
      a first lens positioned at the proximal end of the nozzle chamber; wherein
   the optical adjustment component comprises a second lens;
   wherein connecting the first magnet and first aligner to the second magnet and second aligner is sufficient to position the first lens to be optically concentric with the second lens.

2. The method according to claim 1, wherein coupling the flow cell nozzle to the optical adjustment component comprises inserting three polygonal-shaped protrusions on the flow cell nozzle into three polygonal-shaped notches in the optical adjustment component.

3. The method according to claim 2, wherein the three polygonal-shaped protrusions on the flow cell nozzle are spaced equidistantly apart from each other along the outer edge of the proximal end of the flow cell nozzle.

4. The method according to claim 1, wherein the first magnet and second magnet are disk-shaped.

5. The method according to claim 4, wherein connecting the first magnet to the second comprises positioning the first magnet to be concentric with the second magnet.

6. The method according to claim 1, wherein the optical adjustment component is non-releasably integrated into a flow cytometer.

7. An optically aligned light collection system comprising:
   flow cell nozzle comprising:
      a nozzle chamber having a proximal end and a distal end;
      a first lens, a first aligner and a first magnet positioned at the proximal end of the flow cell nozzle; and
      a nozzle orifice positioned at the distal end of the nozzle chamber; and
   an optical adjustment component comprising:
      a second lens;
      a second aligner; and
      a second magnet,
   wherein the first lens is optically concentric with the second lens when the first aligner is coupled to the second aligner and the first magnet is connected to the second magnet.

8. The system according to claim 7, wherein the first aligner is an alignment component selected from the group consisting of a protrusion, a groove, a notch and a hole.

9. The system according to claim 8, wherein the first aligner is a polygonal-shaped protrusion.

10. The system according to claim 7, wherein the second aligner is an alignment component selected from the group consisting of a protrusion, a groove, a notch and a hole.

11. The system according to claim 10, wherein the second aligner is a polygonal-shaped notch.

12. The system according to claim 7, wherein the flow cell nozzle and optical adjustment component each comprise three aligners and three magnets.

13. The system according to claim 12, wherein:
the three aligners are spaced equidistantly apart from each other along the outer edge of the proximal end of the flow cell nozzle; and
the three magnets are spaced equidistantly apart from each other along the outer edge of the proximal end of the flow cell nozzle.

14. The system according to claim 7, wherein the second lens is a focusing lens.

15. The system according to claim 7, wherein the first magnet and the second magnet are disk shaped.

16. The system according to claim 15, wherein the first magnet is concentric with the second magnet when the first aligner is coupled to the second aligner.

17. The system according to claim 7, wherein the optical adjustment component is non-releasably integrated into a flow cytometer.

18. The system according to claim 7, wherein the flow cell nozzle further comprises one or more fluid ports.

19. The system according to claim 18, wherein the flow cell nozzle comprises a sample injection port and a sheath fluid port.

\* \* \* \* \*